United States Patent
Finiels et al.

(10) Patent No.: US 6,552,003 B2
(45) Date of Patent: *Apr. 22, 2003

(54) MUSCLE REINNERVATION AND MOTOR AXON SPROUTING BY ADMINISTERING DNA SEQUENCES ENCODING NT-3 AND CNTF

(75) Inventors: Françoise Finiels, Tarne (FR); Minerva Gimenez-Ribotta, Montpellier (FR); Jacques Mallet, Paris (FR); Alain Privat, Saint Clement de Riviere (FR); Frédéric Revah, Paris (FR)

(73) Assignees: Aventis Pharma S.A., Antony (FR); Institut National de la Sante et de la Recherche Medicale (INSERM), Paris (FR)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/356,032

(22) Filed: Jul. 16, 1999

(65) Prior Publication Data

US 2002/0164303 A1 Nov. 7, 2002

Related U.S. Application Data

(63) Continuation of application No. PCT/EP98/00220, filed on Jan. 16, 1998, and a continuation-in-part of application No. 08/785,074, filed on Jan. 17, 1997
(60) Provisional application No. 60/042,247, filed on Mar. 31, 1997.

(51) Int. Cl.$^7$ ............................................... A01N 43/04
(52) U.S. Cl. ..................... 514/44; 424/93.2; 424/93.6; 435/320.1
(58) Field of Search ..................... 435/320.1; 514/44; 424/93.2, 93.6

(56) References Cited

U.S. PATENT DOCUMENTS 5,580,859 A * 12/1996 Felgner et al. ................ 514/44

FOREIGN PATENT DOCUMENTS

| WO | WO 91/03569 | * 3/1991 |
| WO | WO 96/18740 | 6/1996 |
| WO | WO 96/27672 | 9/1996 |
| WO | WO 97/39629 | 10/1997 |

OTHER PUBLICATIONS

Sahenk et al (1993) Brain Res. 606, 126–129.*
Science (1995) 269, 1050–1055.*
Sendtner et al (1992) Nature 358, 502–504.*
Blau (Nov. 2, 1995) The New England J. Med., 1204–1207.*
Ridoux et al (1994) Brain Research 648, 171–175.*
Henderson (1995) Pathogen. Therapy ALS, Advances in Neurobiology, vol. 68, pp 235–240.*
Treco et al (1995) Molec. Med. Today, vol. 1, pp. 314–321.*
Ghadge et al., CNS gene delivery by retorgrade transport of recombinant replication–defective adenoviruses, Gene Therapy, vol. 2: 132–37 (1995).
Kahn et al., Thérapie génique des maladies neurologiques, C. R. Soc. Biol., vol. 190: 9–11 (1996).
Haase et al., Gene therapy of murine motor neuron disease using adenoviral vectors for neurotrophic factors, Nature Medicine, vol. 3: 429–36 (1997).

* cited by examiner

*Primary Examiner*—Deborah Crouch
(74) *Attorney, Agent, or Firm*—Finnegan, Henderson, Farabow, Garrett, & Dunner LLP

(57) ABSTRACT

The present invention relates to methods and compositions for delivering nucleic acids to motor neurons by administering the nucleic acids to muscle tissue. The invention relates to methods for treating pathologies of the nervous system, such as trauma and neurodegenerative diseases.

45 Claims, 12 Drawing Sheets

MUSCLE REINNERVATION AND MOTOR AXON SPROUTING BY ADMINISTERING DNA SEQUENCES ENCODING NT-3 AND CNTF

CROSS REFERENCE TO RELATED APPLICATION

This application is CON of PCT/EP98/00220, filed Jan. 16, 1998 and is a CIP of Ser. No. 08/785,074, filed Jan. 17, 1997 and claims benefit of 60/042,247, filed Mar. 31, 1997.

FIELD OF THE INVENTION

The present invention relates to methods of delivering a nucleic acid to motor neurons comprising administering the nucleic acid to muscle tissue. More particularly, the invention relates to methods for treating pathologies of the nervous system by intramuscular administration of a therapeutic gene, and gene transfer into medullary motor neurons. This invention also relates to compositions comprising the gene in a form suitable for intramuscular administration.

BACKGROUND OF THE INVENTION

Neurodegenerative Disease

Motor neuron diseases, such as amyotrophic lateral sclerosis (ALS) and spinal muscular atrophy of infancy (SMA), are often debilitating and resist curative treatment. For example, ALS is heavily disabling and invariably lethal. With an incidence of 2.5/100 000 in constant increase, a prevalence of 6–10/100,000 (Leigh, Pathogenic mechanisms in amyotrophic lateral sclerosis and other motor neurons disorders in Neurodegenerative diseases by CALNE, Saunders W. B. Eds, Philadelphia, U.S.A., 1994), ALS affects 90,000 patients in developed countries, mostly adults in their sixth decade. The disease is characterized by a progressive motor neuron degeneration leading to paralysis, to total loss of motor and respiratory functions, and eventually to death two to eight years after the appearance of the first clinical signs (mean duration after onset three years). ALS is of genetic origin in 5% of the patients, and sporadic in 95% of the cases. Point mutations in the gene encoding for Cu/Zn superoxide dismutase (SOD1) localised on chromosome 21q22-1 are responsible for the pathology in 20% of the familial cases (Rosen et al., Mutations in Cu/Zn superoxide dismutase gene are associated with familial amyotrophic lateral sclerosis, Nature, 362, 59–62, 1993, review in Rowland, Amyotrophic lateral sclerosis: Human challenge for neuroscience, Proc. Natl. Acad. Sci. USA, 92, 1251–1253, 1995). The pathophysiological basis of the sporadic forms remains unknown. Although the use of Rilutek provides ALS patients with a modest increase in survival probability, there is no curative treatment available for this disorder.

Spinal muscular atrophy of infancy is an autosomal recessive disease, which in its most severe form (SMA type 1) affects 1/16,000–25 000 infants in Europe and North America. SMA-1 patients manifest weakness before three months of age and are never able to be maintained in a sitting posture. Average life expectancy is 8 months, with 95% mortality before the second birthday (review in Crawford and Pardo, The neurobiology of childhood spinal muscular atrophy, Neurobiol. of Disease, 3, 97–110, 1996). The disease is linked to mutations in the SMN gene (Lefebvre et al., Identification and characterization of a spinal muscular atrophy determining gene, Cell, 80, 155–165, 1995). There is no curative treatment available for this disease.

Neurothrophic Factors

Neurotrophic factors have been suggested as potential therapeutic agents for motor neuron diseases (Thoenen et al., Exp. Neurology 124,47–55, 1993). Indeed, embryonic motor neuron survival in culture is enhanced by members of the neurotrophin family such as brain derived neurotrophic factor (BDNF), neurotrophin-3 (NT-3), NT-4 (NT-4/5), cytokines such as ciliary neurotrophic factor (CNTF), leukaemia inhibitory factor (LIF) and cardiotrophin-1, glial cell line-derived neurotrophic factor (GDNF), insulin-like growth factor-1 (IGF-1) and members of the FGF family (review in Henderson, Neurotrophic factors as therapeutic agents in amyotrophic lateral sclerosis: potential and pitfalls. In Serratrice G. T. and Munsat T. L. eds. *Pathogenesis and therapy of amyotrophic lateral sclerosis.* Advances in Neurology, 68, pp. 235–240, 1995. Lippincott-Raven publishers, Philadelphia; Pennica et al., Cardiotrophin-1 a cytokine present in embryonic muscle, supports long-term survival of spinal motoneurons. Neuron, 17, 63–74, 1996).

In vivo, a reduction of motoneuronal death occurring naturally during embryonic development was observed with CNTF (Oppenheim et al., Control of embryonnic motoneuron survival in vivo by ciliary neurotrophic factor. Science, 251, 1616–1618, 1991), BDNF (Oppenheim et al., Brain-derived neurotrophic factor rescues developing avian motoneurons from cell death. Nature, 360, 755–757, 1992), GDNF (Oppenheim et al., Developing motor neurons rescued from programmed and axotomy-induced cell death by GDNF. Nature, 373, 344–346, 1995), and cardiotrophin-1 (Pennica et al., 1996). Protection from retrograde motor neuron death after acute peripheral nerve axotomy in neonate rodents was evidenced with several factors (Sendtner et al., Ciliary neurotroptuc factor prevents the degeneration of motor neurons after axotomy, Nature 345, 440–441, 1990, Sendtner et al., Ciliary neurotrophic factor prevents degeneration of motor neurons in mouse mutant progressive motor neuronopathy. Nature, 358, 502–504, 1992; Sendtner et al., Brain-derived neurotrophic prevents the death of motoneurons in newborn rats after nerve section. Nature, 360, 757–759, 1992; Vejsada et al., Quantitative comparison of the transient rescue effects of neurotrophic factors on axotomised motoneurons in vivo. Eur. J. Neurosci., 7, 108–115, 1995). Also, a protective effect of CNTF and/or BDNF was described in two murine models of inherited progressive motor degeneration (Sendtner et al., 1992; Mitsumoto et al., Arrest of motor neuron disease in wobbler mice cotreated with CNTF and BDNF. Science, 265, 1107–1110, 1994).

Data showing that neurotrophic factors enhance motoneuronal survival under multiple experimental conditions, suggest that these molecules could decrease the vulnerability of motoneurons in human pathologies. However the use of trophic factors in patients is limited by their poor bioavailaility after systemic administration.

Neurotrophic factors systemically administered penetrate the nervous system with low yield because of the presence of the blood-brain barrier. Only a very small fraction of the injected factor reaches motoneurons, most probably at the level of neuromuscular synapses (Dittrich et al., Ciliary neurotrophic cancer: pharacokinetics and acute phase response. Ann. Neurol., 35, 151–163, 1994, Yan et al., 1994). Furthermore trophic factors are rapidly degraded and display a short half-life after systemic administration (2.9 minutes for CNTF in rat Dittrich et al., 1994, Cedarbaum et al., A double-blind placebo-controlled clinical trial of subcutaneous recombinant human ciliary neurotrophic factor (rHCNTF) in amyotrophic lateral sclerosis. Neurology, 46, 1244–1249, 1996). As a consequence high doses have to be administered in order to have any possibility of reaching therapeutic concentrations at the motoneuronal levels. However, such doses are likely to produce negative side effects. This has been illustrated in clinical trials using recombinant CNTF injected to ALS patients. The injected doses shown to produce a therapeutic effect in animals (Mitsumoto et al, 1994) were above toxicity threshold in human (Miller et al., A placebo-controlled trial of recombinant human ciliary neurotrophic (rhCNTF) factor in amyotrophic lateral sclerosis. Annals Neurol., 39, 256–260, 1996), and adverse effects such as cough, asthenia, nausea, weight loss and even increased death rate at the highest dose were observed, while no beneficial effect of CNTF treatment could be detected (Miller et al., 1996).

The clinical use of neurotrophic factors thus requires the development of suitable modes of in vivo delivery. Therapeutic gene transfer offers potential advantages over direct administration of the protein, such as continuous and/or targeted production of the desired transgene in vivo.

Gene Therapy

Gene therapy is rapidly emerging as an effective approach for management and treatment of a variety of diseases. Examples of effective gene therapy regimens appear routinely in the literature (see for example Roth et al., Nature Medicine, Vol. 2, 985–991 (1996)).

Gene therapy, including the administration of modified viruses as vectors, constitutes a particularly promising approach for treating neurodegenerative diseases. Among the viruses in current use for gene therapy are adenoviruses (Le Gal La Salle et al., Science 259, 988–990), herpes viruses, adeno-associated viruses and retroviruses. Studies have shown that these vectors, and in particular the adenoviruses, are capable of infecting with a very high efficiency cells of the central nervous system. These results have enabled the development of methods for treating pathologies of the central nervous system by direct injection into the central nervous system (in particular by stereotaxis) of recombinant adenoviruses comprising a therapeutic gene (see WO94/08026, the contents of which are incorporated herein by reference).

With respect to neurodegenerative diseases or traumas associated with the spinal cord, gene therapy provides a method to combat degeneration of the motor neurons (motoneurons) by delivering therapeutic genes, such as a gene encoding a neurotrophic factor or a growth factor to motor neurons. However, prior methods are limited by the lack of a simple method enabling specific transfer of a gene into motor neurons. The present invention overcomes this problem.

SUMMARY OF THE INVENTION

The present invention describes a particularly efficient method for the selective transfer of genes into motor neurons.

One aspect of the invention provides a method of delivering a nucleic acid to mammalian motor neurons comprising administering said nucleic acid to muscle tissue, wherein said nucleic acid is delivered to said motor neurons.

Another aspect of the invention is a method of delivering a nucleic acid to mammalian motor neurons comprising administering said nucleic acid to muscle tissue proximate to the site of a nerve linkage associated with a chosen medullary functional level, wherein said nucleic acid is delivered to said motor neurons.

Another aspect of the invention is a method of producing a protein in mammalian motor neurons comprising administering a nucleic acid encoding said protein to muscle tissue, wherein said nucleic acid is delivered to said motor neurons and expressed. In a preferred embodiment, the protein is produced at the post synaptic ends of neuromuscular junctions.

The invention also provides a method of inducing peripheral or collateral sprouting of motor axon endings comprising administering a nucleic acid to muscle tissue, wherein said nucleic acid induces peripheral or collateral sprouting of motor axon endings. In a preferred embodiment, the nucleic acid encodes a protein, such as a neurotrophic factor or a growth factor.

Another aspect of the invention is a method of protecting against axonal degeneration comprising administering a nucleic acid to mammalian muscle tissue, wherein said nucleic acid is delivered to said motor neurons and protects against axonal degeneration.

Still another aspect of the invention is a method of treating an impairment of the nervous system comprising administering a nucleic acid encoding a neuroactive substance to mammalian muscle tissue, wherein said nucleic acid is delivered to motor neurons. Preferred embodiments are the treatment of nerve damage and neurodegenerative diseases, such as amyotrophic lateral sclerosis and spinal muscular atrophy of infancy.

A preferred aspect of the invention is a method of treating amyotrophic lateral sclerosis comprising administering to muscle tissue of a mammal suffering therefrom a replication defective adenovirus comprising a gene encoding neurotrophin-3.

Panel A: Comparison of naked DNA to adenovirus.

Panel B: Impact of batch preparation.

Panel C: Comparison of CMV and RSV promoters in new-born mice.

Panel D: Comparison of CMV and RSV promoters in adult mice.

Figure 8:
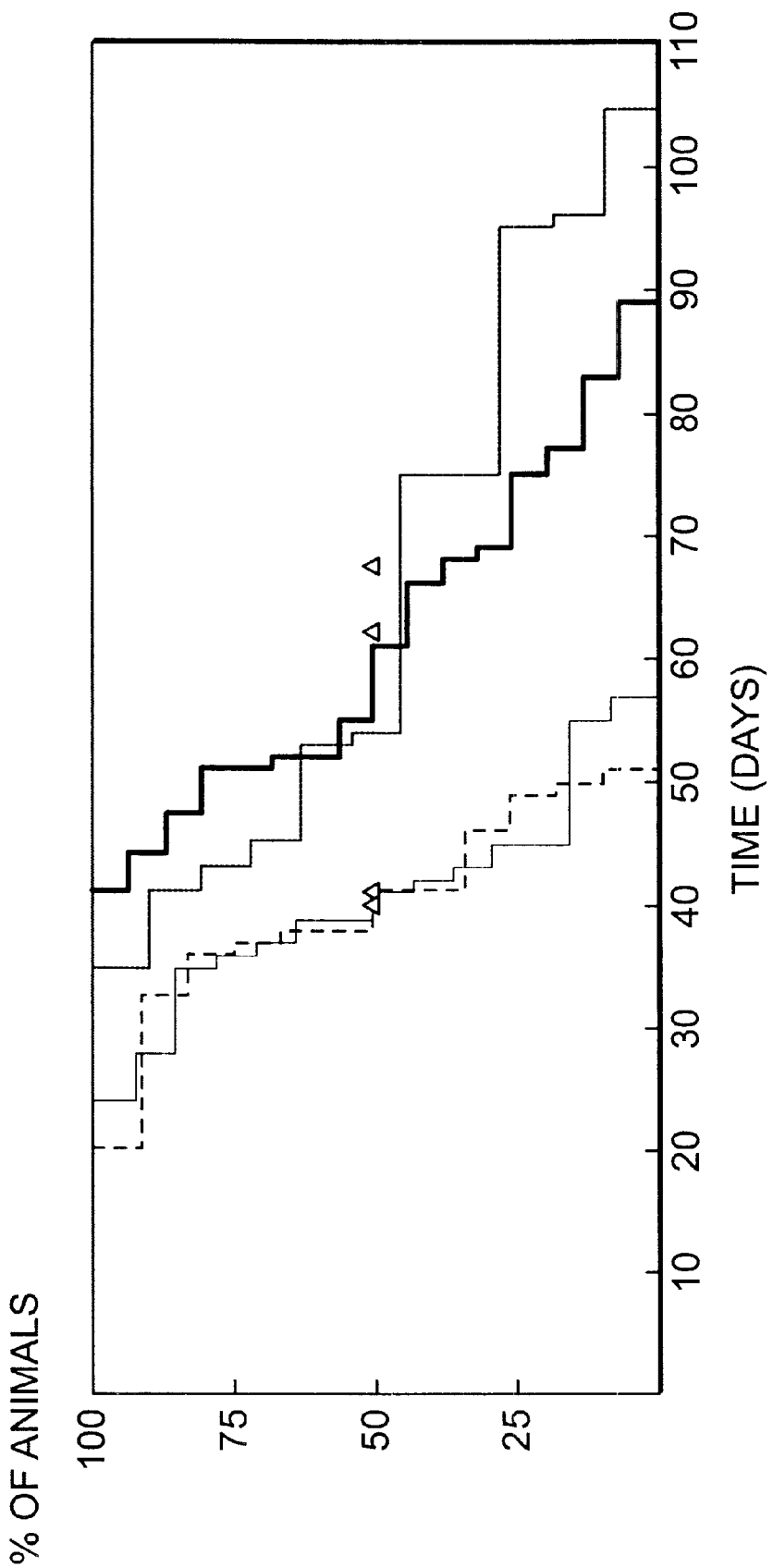

FIG. 8: Survival of pmn-mice after AdNT-3±AdCNTF Intramuscular Injection

Suvival of pmn-mice in each treatment group is expressed as a percentage of investigated animals (100%). Survival of AdNT-3-treated animals (bold line; n=16) and AdNT-3+ AdCNTF cotreated animals (grey line; n=11) is significantly different (p<0.005) from non-treated (solid line; n=14) or AdlacZ vector injected mice (dashed line; n=12). Triangles: mean time of survival.

Figure 9:
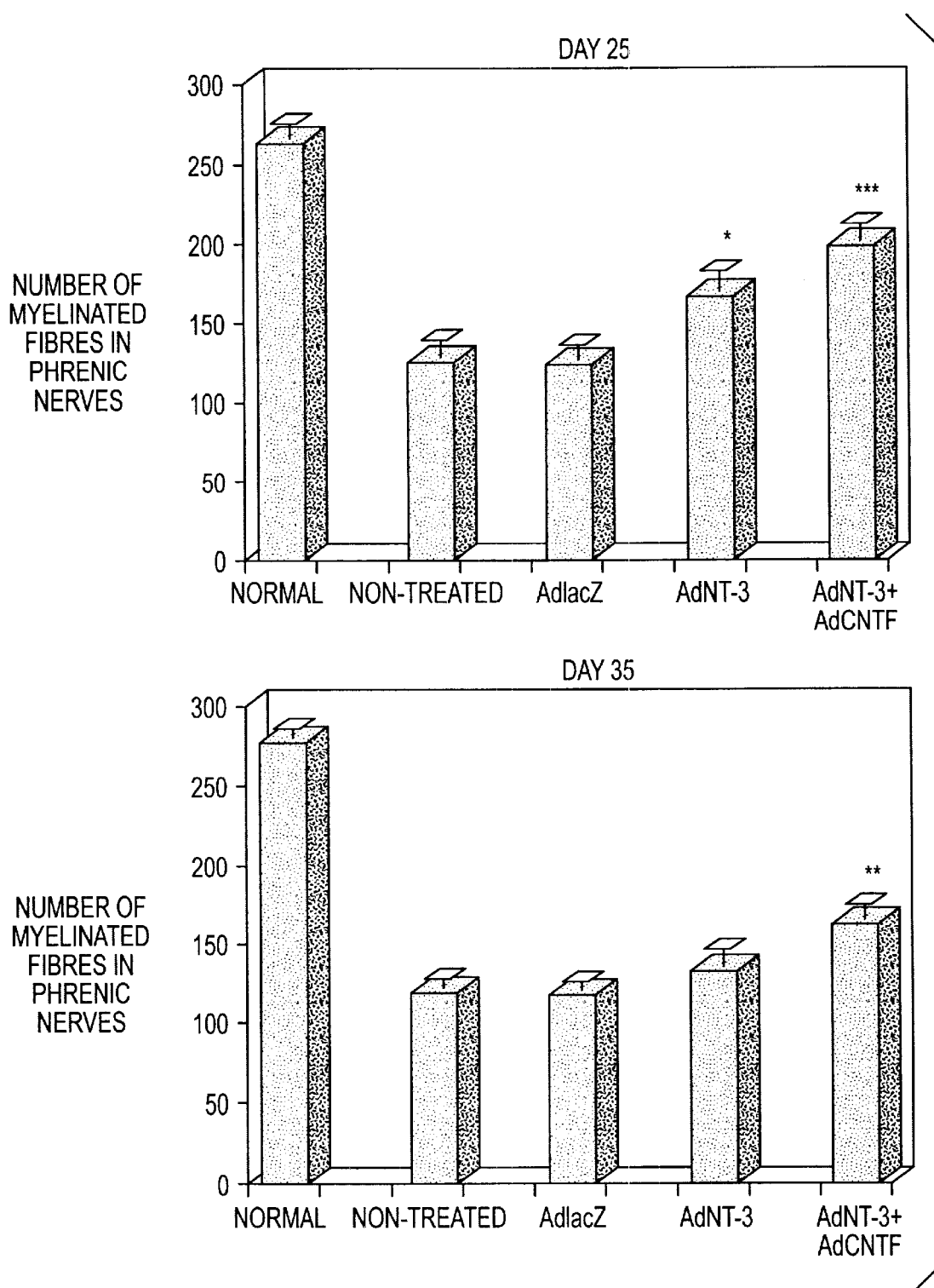
Figure 10A:
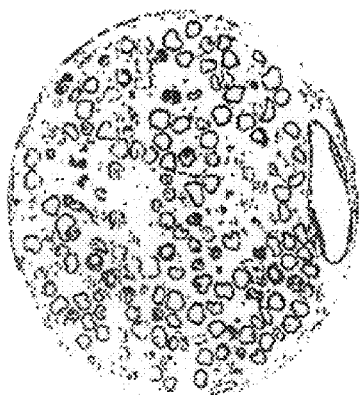
Figure 10B:
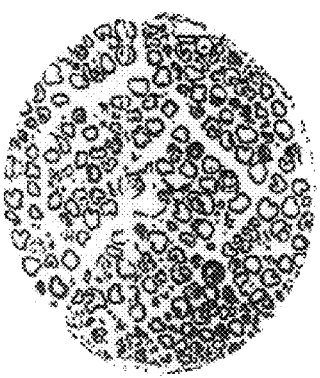
Figure 10C:
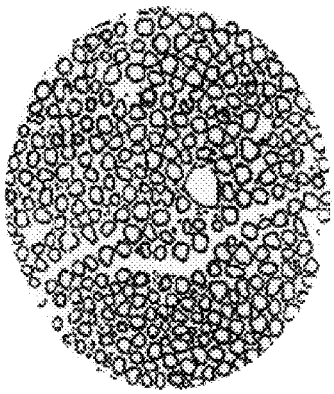
Figure 10D:
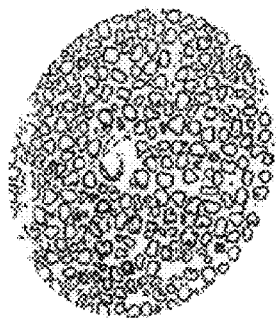
Figure 10E:
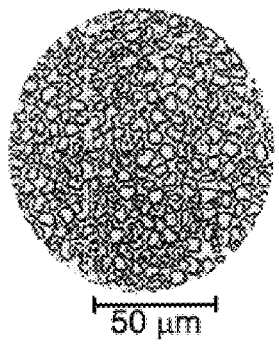
Figure 10F:
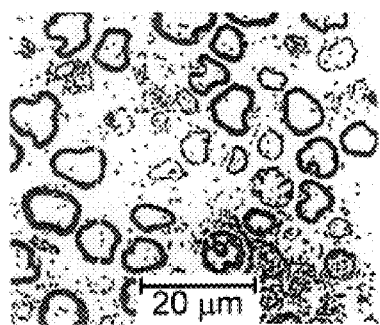
Figure 10G:
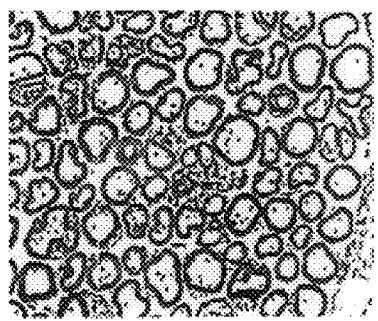

FIG. 9: Number of myelinated fibers in phrenic nerves after AdNT-3±AdCNTF treatment.

At day 25 the number of myelinated fibers in phrenic nerves of non-treated and AdlacZ-injected pmn-mice was much smaller (122, n=8 and 120, n=6, respectively) than in non-affected littermates (263, n=4). The nerves of treated pmn-mice, however, contained more myelinated fibers than those of non-treated pmn-mice (AdNT-3: 164, n=8, *, p<0.05; AdNT-3+AdCNTF: 192, n=8, *, p<0.001). Also at day 35, the number of myelinated fibres was higher in AdNT-3+AdCNTF-treated (157, n=10, p<0.01, ) than in non-treated (118, n=10) or AdlacZ-injected pmn-mice (115, n=8); this corresponds to a reduction in fiber loss by 20%. At this age the difference between pmn-mice that had been treated with AdNT-3 alone (130, n=7) and all control animals (n=18) was of borderline significance (p=0.054). Small bars indicated SEM.

FIG. 10(A–E): Electronmicrographs of phrenic nerves from AdNT-3±AdCNTF-treated pmn-mice aged 25 days.

A: Non-treated pmn-mouse; B: AdlacZ-treated pmn-mouse; C: Normal litter mate; D: AdNT-3-treated pmn-mouse; E: AdNT-3+AdCNTF-treated pmn-mouse; F–G: High-power views of nerves from non-treated (F) and AdNT-3+AdCNTF-treated pmn-mice (G). Note increased number of myelinated axons in treated (D,E,G) as compared to non-treated (A,B,F) pmn-mice. The axons in treated mice tended to be smaller than in normal and also in non-treated pmn-mice; the cross-sectional area of the nerve in non-treated pmn-mice was often larger than in treated pmn-mice which reflected proliferation of Schwann cells and formation of Bungner bands (A,F).

FIG. 11(A–F): Terminal innervation pattern in muscles from treated and non-treated pmn-mice.

Superficial gluteus muscles of pmn-mice (e–f) and non-affected littermates (a,b) aged 4 weeks stained with an acetylcholinesterase-silver method. a: Overview of the endplate zone showing numerous enplates supplied by long terminal axons. The sensory innervation of a muscle spindle is also visible (left). b: Bundle of five long axons emerging from a small nerve branch and supplying 5 endplates. The axons of two endplates closest to the nerve branch can only be followed for short distances. c: Non-treated pmn-mouse. An overview of the endplate zone shows loss of terminal axons and isolated enplates. The nerve branch consists of two axons only and contains debris of degenerated axons. d: Non-treated pmn-mouse. Bundle of terminal axons in a relatively well-preserved part of the muscle. The innervation pattern resembles that in a normal mouse (b), but the axons are irregularly shaped and the terminal branches are rarified. e: AdNT3-treated pmn-mouse. One terminal axon emerging from a nerve branch (left) branches at two successive Ranvier nodes and forms 3 and 4–5 branches, respectively (arrows), and supplies a group of endplates. f: AdNT3+AdCNTF-treated pmn-mouse. Three terminal axons branch repeatedly and supply a large number of endplates. The last Ranvier node of one of these axons gives rise to three short branches which supply three endplates, one of which by means of a terminal sprout supplies a fourth endplate (arrow). Calibration bar: 100 µm (a,e) and 25 µm (b, d–f).

DETAILED DESCRIPTION OF THE INVENTION

The present invention describes a particularly efficient method for the selective transfer of genes into motor neurons. The invention demonstrates that it is possible to specifically transfer a gene into the motor neurons by administration into the muscle. Applicants describe herein that adenoviruses are advantageously absorbed at the level of the neuromuscular junctions (motor endplates), and transported up to the cellular bodies of the motor neurons (ventral horn of the spinal cord) by retrograde transport along the motoneuronal axons. Intramuscular injections of recombinant adenoviruses expressing a trophic factor provides a particularly attractive mode of administration. After intramuscular injection adenoviruses will infect myotubes, thus allowing the trophic factor to be produced at the synaptic end of motoneurons and to be released continuously in the circulation. Intramuscular injections lead to retrograde transport of injected recombinant adenoviruses, allowing high yield infection of the afferent motoneurons (Finiels et al., Specific and efficient gene transfer strategy offers new potentialities for the treatment of motor neurone diseases. Neuroreport, 7, 373–378, 1995). This leads to the production of the transgene within the spinal cord.

Intramuscular administration of a therapeutic gene constitutes a new and very specific method for infecting the motor neurons by retrograde transport. The present invention enables one to target precisely the medullary stage on which it is desired to act, according to the location of the trauma and/or of the degeneration. In particular, the present invention advantageously enables one to specifically and unilaterally infect the motor neurons of the different medullary functional stages by following the precise map of the neuromuscular junctions. The present invention has been found to be less traumatic and more specific than stereotaxic injection into the medullary parenchyma, which is more diffuse and not restricted to the motor neurons.

Definitions

The following defined terms are used throughout the present specification, and should be helpful in understanding the scope and practice of the present invention.

A "polypeptide" is a polymeric compound comprised of covalently linked amino acid residues. Amino acids have the following general structure:

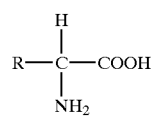

Amino acids are classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

A "protein" is a polypeptide which plays a structural or functional role in a living cell.

The polypeptides and proteins of the invention may be glycosylated or unglycosylated.

A "variant" of a polypeptide or protein is any analogue, fragment, derivative, or mutant which is derived from a polypeptide or protein and which retains at least one biological property of the polypeptide or protein. Different variants of the polypeptide or protein may exist in nature. These variants may be allelic variations characterized by differences in the nucleotide sequences of the structural gene coding for the protein, or may involve differential splicing or post-translational modification. The skilled artisan can produce variants having single or multiple amino acid substitutions, deletions, additions, or replacements. These variants may include, inter alia: (a) variants in which one or more amino acid residues are substituted with conservative or non-conservative amino acids, (b) variants in which one or more amino acids are added to the polypeptide or protein, (c) variants in which one or more of the amino acids includes a substituent group, and (d) variants in which the polypeptide or protein is fused with another polypeptide such as serum albumin. The techniques for obtaining these variants, including genetic (suppressions, deletions, mutations, etc.), chemical, and enzymatic techniques, are known to persons having ordinary skill in the art.

If such allelic variations, analogues, fragments, derivatives, mutants, and modifications, including alternative mRNA splicing forms and alternative post-translational modification forms result in derivatives of the polypeptide which retain any of the biological properties of the polypeptide, they are intended to be included within the scope of this invention.

A "nucleic acid" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes cDNA, genomic DNA, synthetic DNA, and semi-synthetic DNA. The sequence of nucleotides that encodes a protein is called the sense sequence.

"Regulatory region" means a nucleic acid sequence which regulates the expression of a second nucleic acid sequence. A regulatory region may include sequences which are naturally responsible for expressing a particular nucleic acid (a homologous region) or may include sequences of a different origin (responsible for expressing different proteins or even synthetic proteins). In particular, the sequences can be sequences of eukaryotic or viral genes or derived sequences which stimulate or repress transcription of a gene in a specific or non-specific manner and in an inducible or non-inducible manner. Regulatory regions include origins of replication, RNA splice sites, enhancers, transcriptional termination sequences, signal sequences which direct the polypeptide into the secretory pathways of the target cell, and promoters.

A regulatory region from a "heterologous source" is a regulatory region which is not naturally associated with the expressed nucleic acid. Included among the heterologous regulatory regions are regulatory regions from a different species, regulatory regions from a different gene, hybrid regulatory sequences, and regulatory sequences which do not occur in nature, but which are designed by one having ordinary skill in the art.

A "vector" is any means for the transfer of a nucleic acid according to the invention into a host cell. The term "vector" includes both viral and nonviral means for introducing the nucleic acid into a cell in vitro, ex vivo or in vivo. Non-viral vectors include plasmids, liposomes, electrically charged lipids (cytofectins), DNA-protein complexes, and biopolymers. Viral vectors include retrovirus, adeno-associated virus, pox, baculovirus, vaccinia, herpes simplex, Epstein-Barr and adenovirus vectors. In addition to a nucleic acid according to the invention, a vector may also contain one or more regulatory regions, and/or selectable markers useful in selecting, measuring, and monitoring nucleic acid transfer results (transfer to which tissues, duration of expression, etc.).

"Pharmaceutically acceptable carrier" includes diluents and fillers which are pharmaceutically acceptable for methods of administration, are sterile, and may be aqueous or oleaginous suspensions formulated using suitable dispersing or wetting agents and suspending agents. The particular pharmaceutically acceptable carrier and the ratio of active compound to carrier are determined by the solubility and chemical properties of the composition, the particular mode of administration, and standard pharmaceutical practice.

A "motor neuron" is a neuron which controls the movement of voluntary muscles.

General Molecular Biology

The techniques of recombinant DNA technology are known to those of ordinary skill in the art. General methods for the cloning and expression of recombinant molecules are described in Maniatis (*Molecular Cloning,* Cold Spring Harbor Laboratories, 1982), and in Ausubel (*Current Protocols in Molecular Biology,* Wiley and Sons, 1987), which are incorporated by reference.

Nucleic Acids

The present invention relates to the discovery that instramuscular administration provides a means for delivering a nucleic acid sequence to motor neurons. The nucleic acid of the invention preferably encodes a neuroactive substance; a substance capable of exerting a beneficial effect on nerve cells. It may be a substance capable of compensating for a deficiency in or of reducing an excess of an endogenous substance. Alternatively, it may be a substance conferring new properties on the cells.

The neuroactive substance may be an antisense sequence or a protein. Among the proteins suitable for practice of the invention are growth factors, neurotrophic factors, cytokines, neurotransmitter synthesizing enzymes, enzymes, neurotransmitter receptors and hormone receptors.

Preferably, the growth factor is a colony stimulating factor (G-CSF, GM-CSF, M-CSF, CSF, and the like), fibroblast growth factor (FGFa, FGFb) or vascular cell growth factor (VEGF). Among the neurotrophic factors, the preferred factors are ciliary neurotrophic factor (CNTF), glial cell maturation factors (GMFa, b), GDNF, BDNF, NT-3, NT-5 and the like.

The neurotrophic factor NT-3 is particularly preferred. The complete nucleotide sequence encoding NT-3 is disclosed in WO91/03569, the contents of which are incorporated herein by reference.

Preferred cytokines are the interleukins and interferons. Enzymes included within the scope of the invention are the enzymes for the biosynthesis of neuro transmitters (tyrosine hydroxylase, acetylcholine transferase, glutamic acid decarboxylase) and the lysosomal enzymes (hexosaminidases, arylsulphatase, glucocerebrosidase, HGPRT). The enzymes involved in the detoxification of free radicals (super oxide dismutase I, II or III, catalase, glutathione peroxidase) are preferred. Receptors include the androgen receptors (involved in Kennedy's disease).

These proteins may be used in native form, or in the form of a variant or fragment thereof.

The neuroactive substance may also be an antisense sequence. The down regulation of gene expression using antisense nucleic acids can be achieved at the translational or transcriptional level. Antisense nucleic acids of the invention are preferably nucleic acid fragments capable of specifically hybridizing with a nucleic acid encoding an endogenous neuroactive substance or the corresponding messenger RNA. These antisense nucleic acids can be synthetic oligonucleotides, optionally modified to improve their stability and selectivity. They can also be DNA sequences whose expression in the cell produces RNA complementary to all or part of the mRNA encoding an endogenous neuroactive substance. Antisense nucleic acids can be prepared by expression of all or part of a nucleic acid encoding an endogenous neuroactive substance, in the opposite orientation, as described in EP 140308. Any length of antisense sequence is suitable for practice of the invention so long as it is capable of down-regulating or blocking expression of the endogenous neuroactive substance. Preferably, the antisense sequence is at least 20 nucleotides in length. The preparation and use of antisense nucleic acids, DNA encoding antisense RNAs and the use of oligo and genetic antisense is disclosed in WO92/15680, the contents of which are incorporated herein by reference.

The nucleic acid may be of natural or artificial origin. It may be especially genomic DNA (gDNA), complementary DNA (cDNA), hybrid sequences or synthetic or semisynthetic sequences. It may be of human, animal, plant, bacterial or viral origin and the like. It may be obtained by any technique known to persons skilled in the art, and especially by screening libraries, by chemical synthesis, or alternatively by mixed methods including chemical or enzymatic modification of sequences obtained by screening libraries. It is preferably cDNA or gDNA.

Regulatory Regions

Generally, the nucleic acids of the present invention are linked to one or more regulatory regions. Selection of the appropriate regulatory region or regions is a routine matter, within the level of ordinary skill in the art.

The regulatory regions may comprise a promoter region for functional transcription in the motor neurons, as well as a region situated in 3' of the gene of interest, and which specifies a signal for termination of transcription and a polyadenylation site. All these elements constitute an expression cassette.

Promoters that may be used in the present invention include both constituitive promoters and regulated (inducible) promoters. The promoter may be naturally responsible for the expression of the nucleic acid. It may also be from a heterologous source. In particular, it may be promoter sequences of eucaryotic or viral genes. For example, it may be promoter sequences derived from the genome of the cell which it is desired to infect. Likewise, it may be promoter sequences derived from the genome of a virus, including the adenovirus used. In this regard, there may be mentioned, for example, the promoters of the E1A, MLP, CMV and RSV genes and the like.

In addition, the promoter may be modified by addition of activating or regulatory sequences or sequences allowing a tissue-specific or predominant expression (enolase and GFAP promoters and the like). Moreover, when the nucleic acid does not contain promoter sequences, it may be inserted, such as into the virus genome downstream of such a sequence.

Some promoters useful for practice of this invention are ubiquitous promoters (e.g. HPRT, vimentin, actin, tubulin), intermediate filament promoters (e.g. desmin, neurofilaments, keratin, GFAP), therapeutic gene promoters (e.g. MDR type, CFTR, factor VIII), tissue-specific promoters (e.g. actin promoter in smooth muscle cells), promoters which are preferentially activated in dividing cells, promoters which respond to a stimulus (e.g. steroid hormone receptor, retinoic acid receptor), tetracycline-regulated transcriptional modulators, cytomegalovirus immediate-early, retroviral LTR, metallothionein, SV-40, E1a, and MLP promoters. Tetracycline-regulated transcriptional modulators and CMV promoters are described in WO 96/01313, U.S Pat. Nos. 5,168,062 and 5,385,839, the contents of which are incorporated herein by reference.

Vectors

As discussed above, a "vector" is any means for the transfer of a nucleic acid according to the invention into a host cell. Preferred vectors are viral vectors, such as retroviruses, herpes viruses, adenoviruses and adeno-associated viruses.

Preferably, the viral vectors are replication defective, that is, they are unable to replicate autonomously in the target cell. In general, the genome of the replication defective viral vectors which are used within the scope of the present invention lack at least one region which is necessary for the replication of the virus in the infected cell. These regions can either be eliminated (in whole or in part), be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (on the isolated DNA) or in situ, using the techniques of genetic manipulation or by treatment with mutagenic agents.

Preferably, the replication defective virus retains the sequences of its genome which are necessary for encapsidating the viral particles.

The retroviruses are integrating viruses which infect dividing cells. The retrovirus genome includes two LTRs, an encapsidation sequence and three coding regions (gag, pol and env). The construction of recombinant retroviral vectors has been described: see, in particular, EP 453242, EP178220, Bernstein et al. Genet. Eng. 7 (1985) 235; McCormick, BioTechnology 3 (1985) 689, etc. In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukaemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are disclosed in WO95/02697.

In general, in order to construct recombinant retroviruses containing a nucleic acid sequence, a plasmid is constructed which contains the LTRs, the encapsidation sequence and the coding sequence. This construct is used to transfect a packaging cell line, which cell line is able to supply in trans the retroviral functions which are deficient in the plasmid. In general, the packaging cell lines are thus able to express the gag, pol and env genes. Such packaging cell lines have been described in the prior art, in particular the cell line PA317 (U.S. Pat. No. 4,861,719); the PsiCRIP cell line (WO90/02806) and the GP+envAm-12 cell line (WO89/07150). In addition, the recombinant retroviral vectors can contain modifications within the LTRs for suppressing transcriptional activity as well as extensive encapsidation sequences which may include a part of the gag gene (Bender et al., J. Virol. 61 (1987) 1639). Recombinant retroviral vectors are purified by standard techniques known to those having ordinary skill in the art.

The adeno-associated viruses (AAV) are DNA viruses of relatively small size which can integrate, in a stable and site-specific manner, into the genome of the cells which they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR)

region of approximately 145 bases at each end, which serves as an origin of replication for the virus. The remainder of the genome is divided into two essential regions which carry the encapsidation functions: the left-hand part of the genome, which contains the rep gene involved in viral replication and expression of the viral genes; and the right-hand part of the genome, which contains the cap gene encoding the capsid proteins of the virus.

The use of vectors derived from the AAVs for transferring genes in vitro and in vivo has been described (see WO 91/18088; WO 93/09239; U.S. Pat. No. 4,797,368, U.S. Pat. No. 5,139,941, EP 488 528). These publications describe various AAV-derived constructs in which the rep and/or cap genes are deleted and replaced by a gene of interest, and the use of these constructs for transferring the said gene of interest in vitro (into cultured cells) or in vivo, (directly into an organism). The replication defective recombinant AAVs according to the invention can be prepared by cotransfecting a plasmid containing the nucleic acid sequence of interest flanked by two AAV inverted terminal repeat (ITR) regions, and a plasmid carrying the AAV encapsidation genes (rep and cap genes), into a cell line which is infected with a human helper virus (for example an adenovirus). The AAV recombinants which are produced are then purified by standard techniques.

The invention also relates, therefore, to an AAV-derived recombinant virus whose genome encompasses a sequence encoding a nucleic acid encoding a neuroactive substance flanked by the AAV ITRs. The invention also relates to a plasmid encompassing a sequence encoding a nucleic acid encoding a neuroactive substance flanked by two ITRs from an AAV. Such a plasmid can be used as it is for transferring the nucleic acid sequence, with the plasmid, where appropriate, being incorporated into a liposomal vector (pseudo-virus).

In a preferred embodiment, the vector is an adenovirus vector.

Adenoviruses are eukaryotic DNA viruses that can be modified to efficiently deliver a nucleic acid of the invention to a variety of cell types.

Various serotypes of adenovirus exist. Of these serotypes, preference is given, within the scope of the present invention, to using type 2 or type 5 human adenoviruses (Ad 2 or Ad 5) or adenoviruses of animal origin (see WO94/26914). Those adenoviruses of animal origin which can be used within the scope of the present invention include adenoviruses of canine, bovine, murine (example: Mav1, Beard et al., Virology 75 (1990) 81), ovine, porcine, avian, and simian (example: SAV) origin. Preferably, the adenovirus of animal origin is a canine adenovirus, more preferably a CAV2 adenovirus (e.g. Manhattan or A26/61 strain (ATCC VR-800), for example).

Preferably, the replication defective adenoviral vectors of the invention comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (WO95/02697), the E2 region (WO94/28938), the E4 region (WO94/28152, WO94/12649 and WO95/02697), or in any of the late genes L1-L5.

In a preferred embodiment, the adenoviral vector has a deletion in the E1 region (Ad 1.0). Examples of E1-deleted adenoviruses are disclosed in EP 185,573, the contents of which are incorporated herein by reference. In another preferred embodiment, the adenoviral vector has a deletion in the E1 and E4 regions (Ad 3.0). Examples of E1/E4-deleted adenoviruses are disclosed in WO95/02697 and WO96/22378, the contents of which are incorporated herein by reference. In still another preferred embodiment, the adenoviral vector has a deletion in the E1 region into which the E4 region and the nucleic acid sequence are inserted (see FR94 13355, the contents of which are incorporated herein by reference).

The replication defective recombinant adenoviruses according to the invention can be prepared by any technique known to the person skilled in the art (Levrero et al., Gene 101 (1991) 195, EP 185 573; Graham, EMBO J. 3 (1984) 2917). In particular, they can be prepared by homologous recombination between an adenovirus and a plasmid which carries, inter alia, the DNA sequence of interest. The homologous recombination is effected following cotransfection of the said adenovirus and plasmid into an appropriate cell line. The cell line which is employed should preferably (i) be transformable by the said elements, and (ii) contain the sequences which are able to complement the part of the genome of the replication defective adenovirus, preferably in integrated form in order to avoid the risks of recombination. Examples of cell lines which may be used are the human embryonic kidney cell line 293 (Graham et al., J. Gen. Virol. 36 (1977) 59) which contains the left-hand portion of the genome of an Ad5 adenovirus (12%) integrated into its genome, and cell lines which are able to complement the E1 and E4 functions, as described in applications WO94/26914 and WO95/02697. Recombinant adenoviruses are recovered and purified using standard molecular biological techniques, which are well known to one of ordinary skill in the art.

Pharmaceutical Administration

The process according to the present invention enables one to target precisely the motor neurons of each medullary functional stage. Thus, according to the site of the impairment to be treated, the administration is made into a muscle carrying a nerve linkage with the said site. According to the present invention, it is now possible, by a judicious choice of various injections, to infect specifically and unilaterally a large number of medullary motor neurons distributed over the various levels.

In a preferred embodiment, administration into the muscles of the upper limbs (biceps, triceps) makes it possible to transfer a gene into the motor neurons at the cervical level; administration into the muscles of the thorax (pectoral muscles) makes it possible to transfer a gene into the motor neurons at the thoracic level; or administration into the muscles of the lower limbs (gastrocnemial muscles) makes it possible to transfer a gene into the motor neurons at the lumbar and sacral levels.

Other muscles may of course be used for administration into these motor neurons, and other motor neurons may also be targeted. To this end, it is possible to use precise maps of the neuromuscular junctions in order to determine, depending on the medullar stage targeted, the most appropriate muscle(s) for the administration. Such maps are accessible to persons skilled in the art (see especially Nicholopoulos et al., J. Comp. Neurol. 217, 78–85; Peyronnard et Charon, Exp. Brain Res. 50, 125–132). Depending on the medullar stage which it will prove convenient to infect, one or more muscles known to be innervated by the stage in question can thus be chosen.

The intramuscular administration can be carried out in various ways. According to a first embodiment, it is performed by injection at several points of the same muscle so as to affect a very large number of motor endplates. This embodiment is particularly efficient when the point of insertion of the nerve into the muscle considered is not identifiable. When the point of insertion of the nerve can be located, the administration is advantageously carried out by one or more injections at or near the said point. According to this embodiment, the efficiency of the transfer is greater because a high proportion of vector administered is absorbed at the level of the neuromuscular junction.

In a preferred embodiment of the present invention, the intramuscular administration is carried out by injections at several points of the same muscle.

In another preferred embodiment of the present invention, the intramuscular administration is carried out by injection(s) at or near the point of insertion of the nerve.

A preferred subject of the present invention is a method for the transfer of nucleic acids into motor neurons comprising the muscular administration of an adenoviral vector incorporating the said nucleic acid into its genome. Preferably, the method according to the invention is carried out by injection(s) at several points of the same muscle, or when the point of insertion of the nerve can be located, by one or more injections at the level of or close to the said point.

Pharmaceutical Compositions

For their use according to the present invention, the nucleic acids, either in the form of a vector or naked DNA, are preferably combined with one or more pharmaceutically acceptable carriers for an injectable formulation. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, allow the constitution of injectable solutions.

The preferred sterile injectable preparations can be a solution or suspension in a nontoxic parenterally acceptable solvent or diluent. Examples of pharmaceutically acceptable carriers are saline, buffered saline, isotonic saline (e.g. monosodium or disodium phosphate, sodium, potassium, calcium or magnesium chloride, or mixtures of such salts), Ringer's solution, dextrose, water, sterile water, glycerol, ethanol, and combinations thereof. 1,3-butanediol and sterile fixed oils are conveniently employed as solvents or suspending media. Any bland fixed oil can be employed including synthetic mono- or di-glycerides. Fatty acids such as oleic acid also find use in the preparation of injectables.

The virus doses used for the administration may be adapted as a function of various parameters, and in particular as a function of the site (muscle) of administration considered, the number of injections, the gene to be expressed or alternatively the desired duration of treatment. In general, the recombinant adenoviruses according to the invention are formulated and administered in the form of doses of between $10^4$ and $10^{14}$ pfu, and preferably $10^6$ to $10^{11}$ pfu. The term pfu (plaque forming unit) corresponds to the infectivity of a virus solution, and is determined by infecting an appropriate cell culture and measuring, generally after 15 days, the number of plaques of infected cells. The technique for determining the pfu titre of a viral solution are well documented in the literature.

In a preferred embodiment, the composition comprises an adenovirus comprising the NT-3 gene (AdNT-3) in a concentration of about $1 \times 10^9$ pfu/100 µl.

The nucleic acid can also be administered as a naked DNA. Methods for formulating and administering naked DNA to mammalian muscle tissue are disclosed in U.S. Pat. Nos. 5,580,859 and 5,589,466, the contents of which are incorporated herein by reference.

The compositions according to the invention are particularly useful for administration to motor neurons as described above.

Treatment of Motor Neuron Impairments

The process according to the present invention is particularly advantageous for the treatment of medullary traumas or of motoneuronal degeneration diseases. Medullary traumas correspond more particularly to sections at the level of the motor neurons which deprive them of their afferences coming from the higher centres and cause their degeneration. The transfer of genes encoding growth factors, for example, into the sublesional motor neurons by retrograde transport according to the invention now offers the possibility of reducing or even preventing this degeneration.

Neuropathies of the motor neuron include amyotrophic lateral sclerosis, spinal amyotrophias type I (Werdnig Hoffman disease), type II or III (Kugelberg-Welander disease), bulbar spinal amyotrophias (such as Kennedy's disease). The transfer of genes encoding growth factors or other molecules known to exert a neurotrophic effect on the motor neuron undergoing degeneration according to the present invention also offers a new route for the treatment of this type of pathology.

The efficacy of the process of the invention can be demonstrated on animal models, such as a model of partial or complete section of the spinal cord, (Wobbler mouse—animal model for studying amyotrophic lateral sclerosis (Leestma J. E., Am. J. Pathol., 100, 821–824)); the mnd mouse (motor neuron degeneration: animal model for studying amyotrophic lateral sclerosis (Messer et al., 1992, Genomics. 18, 797–802)); pmn mouse (progressive motor neuron neuropathy: animal model for studying motor neural degeneration during development), and SOD* mice: transgenic mice expressing mutated forms of Cu/Zn SOD responsible for familial forms of amyotrophic lateral sclerosis, as illustrated in the examples. The incorporation, tolerance and safety for man can be tested on in vitro models of culture of human embryonic medullary neurons.

EXAMPLES

The present invention will be described in greater detail with the aid of the following examples which should be considered as illustrative and nonlimiting. Example 1 demonstrates infection and retrograde transport within motor neurons following intramuscular injection using a replication defective adenovirus comprising a marker gene. Example 1 further demonstrates the effect of adenovirus vectors on host immune system and inflammatory responses. Example 2 demonstrates the efficacy of an AdNT-3 in two animal models of amyotrophic lateral sclerosis. Example 3 demonstrates marker gene expression following administration of naked DNA to muscle tissue.

Example 1

Injection of Adenovirus—β-galactosidase into the Gastrocnemial Muscle in Intact Rats or in Rats Having Undergone a Thoracic Hemisection of the Spinal Cord This example describes the transfer of the β-gal gene at the level of the lumbar motor neurons by administration of an adenovirus incorporating the said gene into the gastrocnemial muscle.

More particularly, the study was carried out on a model of partial or complete section of rat spinal cord performed at the low thoracic level which has the effect of paralysing the animal in one or both of its lower limbs. Such a section deprives the motor neurons of their afferences coming from the upper centres and bring about their degeneration. The administration was carried out so as to infect the sublesional motor neurons by retrograde transport.

The adenoviral vector used in this example is the Ad.RSV.βgal vector. This vector lacks sequences necessary for its replication, but comprises the sequences necessary for penetrating into the cells infectable by the said vector as well as all the essential sequences necessary for the encapsidation of this adenovirus. It also carries, under the control of the RSV promoter, the *E. coli* β-galactosidase gene. The construction of the defective recombinant adenovirus Ad.RSVβgal has been described in the literature (Stratford-Perricaudet et al., J. Clin. Invest. 90 (1992) 626). Briefly, the adenovirus Ad.RSVβgal is a defective recombinant adenovirus (from which the E1 and E3 regions have been deleted) obtained by homologous recombination in vivo between the mutant adenovirus Ad-dl324 (Thimmappaya et al., Cell 31 (1982) 543) and the plasmid pAd.RSVβgal (Akli et al., 1993).

The plasmid pAd.RSVβgal contains, in the 5'→3' orientation,

- the PvuII fragment corresponding to the left end of the Ad5 adenovirus comprising: the ITR sequence, the origin of replication, the encapsidation signals and the enhancer E1A;
- the gene encoding β-galactosidase under the control of the RSV promoter (Rous sarcoma virus),
- a second fragment of the Ad5 adenovirus genome which allows homologous recombination between the plasmid pAd.RSVβgal and the adenovirus dl324.

After linearization with the ClaI enzyme, the plasmid pAd.RSVβgal and the adenovirus dl324 are co-transfected into the line 293 in the presence of calcium phosphate in order to allow homologous recombination. The recombinant adenoviruses thus generated are selected by plaque purification. After isolation, the recombinant adenovirus DNA is amplified in the cell line 293, which leads to a culture supernatant containing the unpurified recombinant defective adenovirus having a titre of about $10^{10}$ pfu/ml. The viral particles are then purified by centrifugation on a caesium chloride gradient according to known techniques (see especially Graham et al., Virology 52 (1973) 456). The adenovirus was then used in purified form in a phosphate buffered saline (PBS).

Three injections of adenovirus Ad-RSV-β-gal ($10^7$ pfu per injection) were performed into the gastrocnemial muscle, just after the animal has (or otherwise) undergone a hemisection of the spinal cord (low thoracic level, which has the effect of paralysing the animal in one of its lower limbs). 9 µl of adenovirus are injected per point of injection with a Hamilton syringe.

The animals were sacrificed (perfusion 4% paraformaldehyde) four days after injection, minimum time for the retrograde transport to occur from the muscle to the spinal cord. Three blocks of spinal cord were cut longitudinally at the cervical, thoracic and lumbar levels, into sections 50 µm thick. The sections were treated for revealing the β-galactosidase which makes it possible to visualize the cells which have been infected by the virus. Some sections were furthermore subjected to an anti-Calcitonin Gene Related Peptide (CGRP) immunocytochemistry which makes it possible to specifically label the motor neurons.

The β-galactosidase was revealed using its substrate, X-gal, and the product of the reaction gives a blue colour.

The Calcitonin Gene Related Peptide, CGRP, is a neurotransmitter, a specific marker for the motor neurons. It is revealed by immunocytochemistry with a secondary antibody coupled to peroxidase and as enzyme substrate diaminobenzidine; the product of the reaction gives a chestnut colour.

The revealing of β-galactosidase made it possible to visualize the presence of the infected motor neurons, exclusively at the sublesional lumbar level in the case of the hemisectioned rats, and on the side corresponding to the injection.

Two types of labelling were obtained, a diffuse labelling of the cellular body of a large number of motor neurons, and a more intense labelling of the cellular body and of the neurites of a more limited number of motor neurons (photographs A and B). This difference in labelling intensity is probably due to the fact that only a few motor neurons, very close to the site of injection, were able to absorb the virus intensely.

The anti-CGRP immunocytochemistry coupled to the β-galactosidase revealing made it possible to demonstrate, by a double staining, that practically all the CGRP-positive cellular bodies (i.e. motor neurons) were infected by the virus (photograph C).

Figure 6:
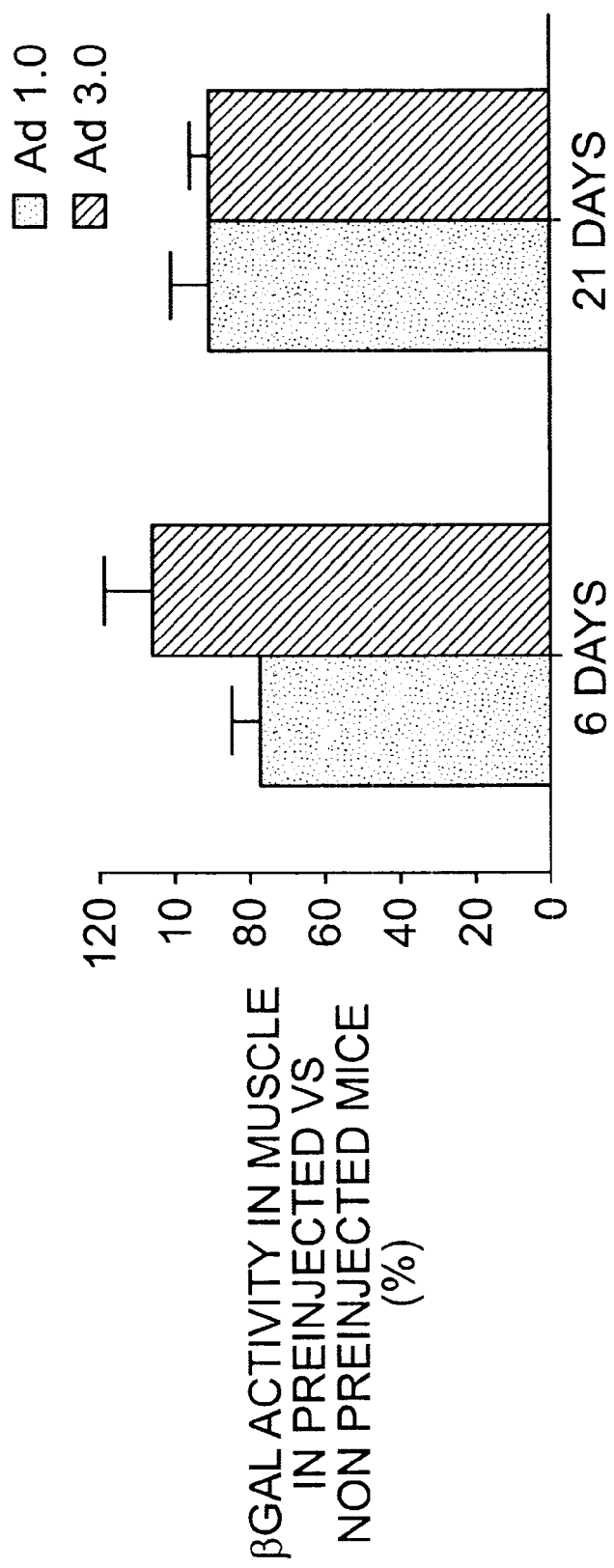
FIG. 6: Immune response following adenoviral injection. β-galactosidase activity in muscle of preinjected and non-preinjected mice.
Figure 7A:
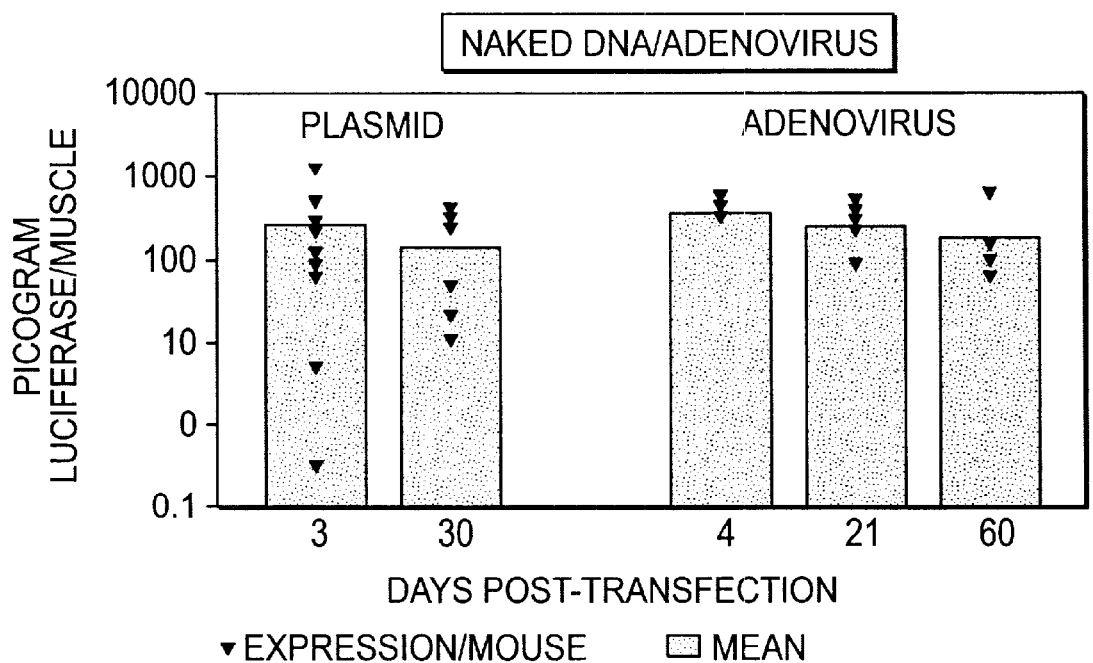
FIG. 7(A–D): Assesment of naked DNA injection.
Figure 7B:
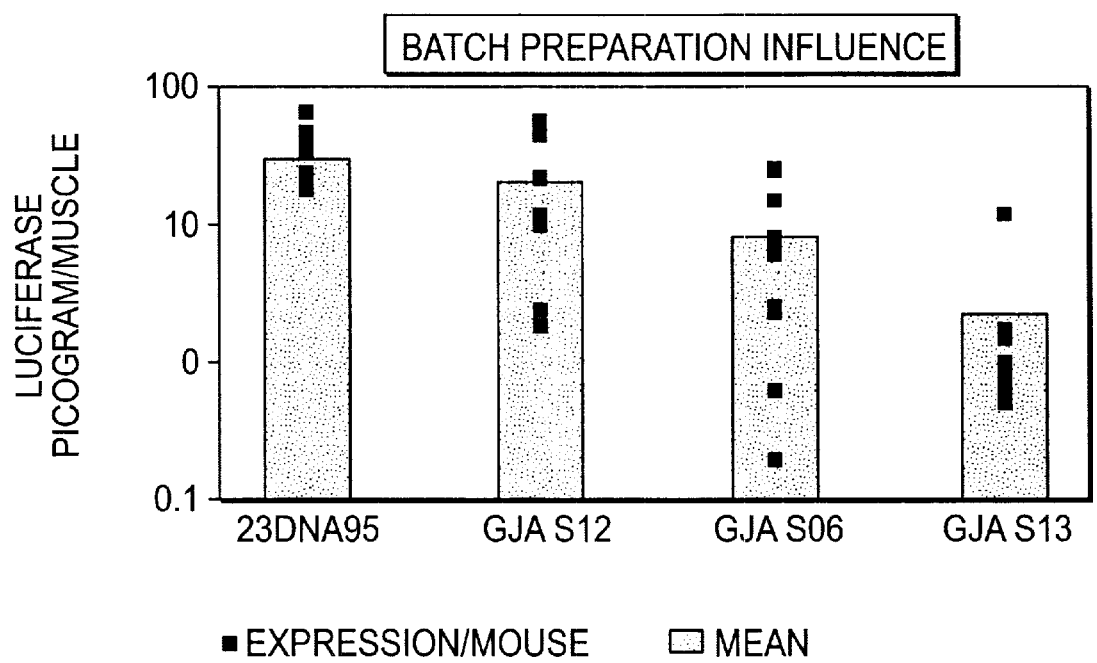
Figure 7C:
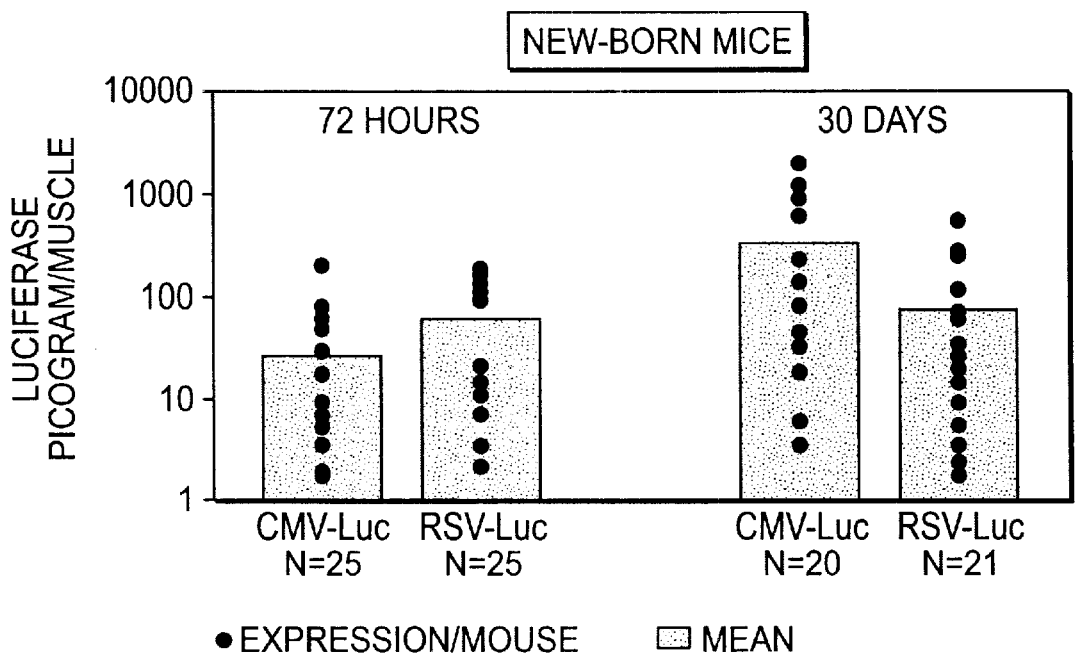
Figure 7D:
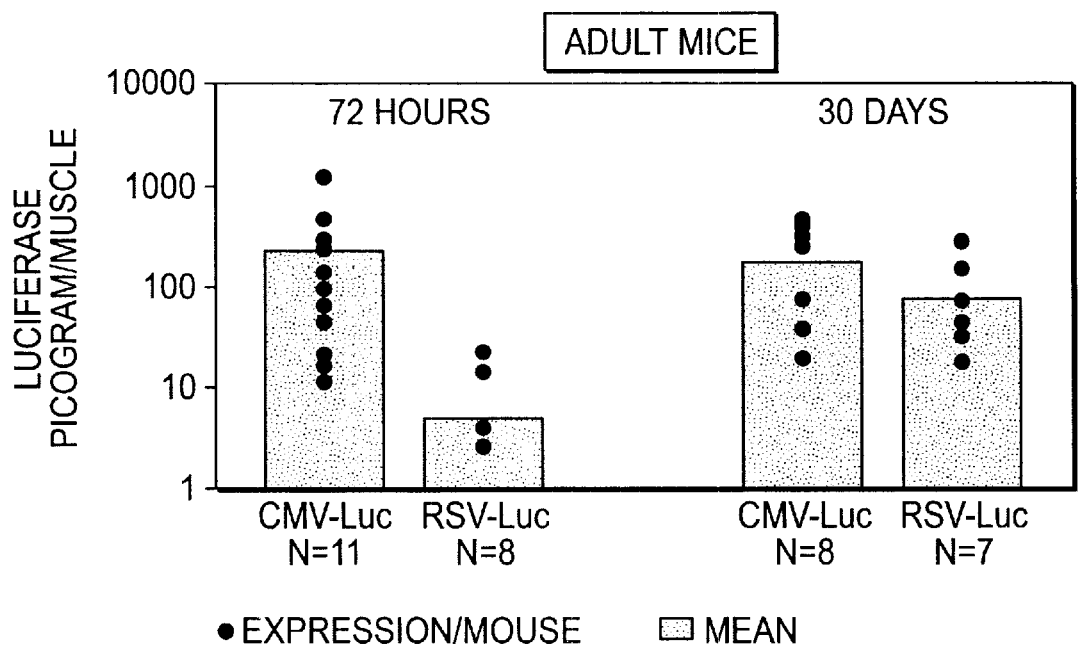

Effect on the Immune/Inflammatory Response After Intramuscular Injection of Adenovirus Immunity:

Epidemiological studies have suggested that as much as 60% of the population over the age of 30 could have antibodies against adenovirus type 5 (Matsuse et al., Immunohistochemical and in situ hybridisation detection of adenovirus early region 1A (E 1A) gene in the microglia of human brain tissue. J. Clin. Pathol., 47, 275–277, 1994). The existence of such a preimmunity in humans could limit the efficiency of recombinant adenovirus injection. In order to test this possibility, mice were preinjected subcutaneously with low doses of a defective Ad-RSVβgal ($10^6$ pfu) in order to preimmunize the animals. Three weeks after the preimmunizing injection, Ad-RSVβgal (2.5 $10^8$ pfu) was administered intramuscularly. One week after intramuscular injection, βgal expression in the muscle was compared in naive animals and preinjected animals. Experiments were done using transgenic animals tolerant for βgal, in order to avoid any immune response against the transgene. Experiments were done using either Ad 1.0 or 3.0 (dllO07) vectors. βgal expression in muscle was quantified by luminometry analysis. The percentage of enzymatic activity observed in preinjected animals as compared to non preinjected animals is shown in FIG. 6.

Conclusion

The data suggest that preinjection affects only in a moderate fashion the efficiency of intramuscular adenoviral gene transfer. Three weeks after intramuscular injection, levels of transgene expression in preinjected animals were 90% that observed in animals that were not preinjected.

Inflammatory Response:

In order to compare the inflammation produced by Ad 1.0 and Ad 3.0, mouse gastrocnemius muscle was injected with $10^9$ tdu of Ad 1.0 E3+ or Ad 3.0 (dllO14) encoding β-galactosidase. Injections were performed using transgenic animals tolerant for βgal, in order to avoid any inflammatory response against the transgene. Two and seven days after injection, no inflammation was visualized in PBS injected muscle. In contrast every Ad-injected muscle displayed a variable number of inflammatory foci, with comparable intensity for Ad 1.0 E3+=Ad 3.0 (n=2 per condition). βgal expression was detected in myofibres, and also in endo- and epimysium. The number of labeled muscle nuclei was higher with Ad 1.0 E3+ than with Ad 3.0.

Conclusion

These short term experiments do not demonstrate an improvement of either inflammatory response or number of labeled cells after i.m. injection of Ad 3.0 as compared to Ad 1.0. However it remains to be investigated whether Ad 3.0 would confer an improved stability of transgene expression on the long term.

Example 2

Examples of the Present Invention in Animals Recognized as Models of Amyotrophic Lateral Sclerosis Animal Models pmn mice: The progressive motor neuropathy (pmn) mutants appeared spontaneously, and the disorder is transmitted in an autosomal recessive fashion (Schmalbruch and Skovgaard-Jensen, Progressive motor neuropathy (pmm), a new neurological mutant in the mouse. Mouse Genome, 87, 113, 1990). The mutated gene is unknown but has been localized on chromosome 6. Homozygous pmn/pmn mice suffer from caudo-cranial motor neuron degeneration and die 5–7 weeks after birth, probably due to respiratory muscle denervation. Detailed histopathological studies of phrenic nerve indicate that the disease is due to a dying back process with distal axon degeneration, and relative preservation of proximal axons and cell bodies (Schmalbruch et al., A new mouse mutant with progressive motor neuropathy. J. Neuropathol. Exp. Neurol., 50, 192–204, 1991). Electromyographical analysis (Kennel et al., Neuromuscular function impairment is not caused by motor neurone loss in FALS mice: an electromyographical study. Neuroreport, 7, 1427–1431, 1996; Kennel et al., Electromyographical and motor performance studies in thepmn mouse model of neurodegenerative disease. Neurobiology of Disease, 3, 137–147, 1996) shows that pmn mice present characteristic features found in ALS patients such as a pure neurogenic pattern, the presence of fibrillations, decreased motor conduction velocity. In contrast, other ALS features such as enlargement of motor unit action potential are not observed in pmn mice.

SOD* mice: Transgenic mice expressing mutated forms of Cu/Zn SOD responsible for familial forms of ALS have been constructed. Animals overexpressing human SOD carrying a substitution glycine to alanine at amino acid position 93 (SOD*) display a progressive motoneuronal degeneration leading to paralysis and death at 4–6 months of age (Gurney et al., Motor neuron degeneration in mice expressing a human Cu, Zn superoxide dismutase mutation. Science, 264, 1772–1775, 1994). First clinical signs consist of fine limb tremor around 90 days of age, followed by a reduction in stride length at 125 days (Chiu et coll., 1995). Histological studies reveal the appearance of vacuoles of mitochondrial origin around day 37, and a loss of motoneurons from day 90 (Chiu et al., Age-dependant penetrance of disease in a transgenic model of familial amyotrophic lateral sclerosis. Mol. Cell. Neurosci., 6, 349–362, 1995). Compensatory collateral reinervation can be observed at the level of neuromuscular junctions (Chiu et al., 1995). SOD* mice display all electrophysiological Lambert's criterias which characterize ALS (Kennel et al., 1996). However the poor therapeutical effect of riluzole on SOD* mice suggests that they could represent the most severe forms of the disease.

AdNT-3 Construct:

The mouse NT-3 gene is isolated as a 1045 bp PCR-fragment encompassing the complete NT-3 preprosequence and cloned into the EcoRV site of a shuttle plasmid containing the inverted terminal repeat (ITR) of the adenoviral genome, encapsidation sequences and adenoviral sequences necessary for subsequent homologous recombination. Transcription of NT-3 is controlled by the Rous Sarcoma Virus (RSV) LTR promoter and terminated by poly A signals present in the NT-3 gene and in the 3' adjacent adenoviral pIX gene. The replication-deficient adenoviral vector AdNT-3 is deleted in regions E1 and E3, and is obtained by in vivo homologous recombination of the linearized pAdNT-3 plasmid with the ClaI-restricted genome of AdRS-VBgal (Stratford-Perricaudet et al., Widespread long term gene transfer to mouse skeletal muscles and heart. J. Clin. Invest. 90, 626–630, 1992).

Example 2A

Administration of Adenovirus Encoding NT3 Into Muscle of pmn Mice pmn-mice were injected with an adenoviral vector encoding murine NT-3 under the control of an RSV promoter, such as described above, at age 3–5 days. The adenoviral dose ($10^9$ pfu in 100 $\mu$l per animal) was unilaterally injected into three muscle groups, the gastrocnemius, the triceps brachii muscle and the long muscles of the thoracic trunk.

Transgene expression after injection procedure was first tested using an adenoviral vector (Adluc) coding for the firefly luciferase gene. At day 25, more than 99% of luciferase activity was found in the injected muscle groups with only marginal activity detected in liver (0.4%), heart (0.1%) and lung (0.1%) and no activity found in diaphragm and spleen.

After administration of the Ad-NT3 vector, adenoviral NT-3 transcripts were detected in the injected gastrocemius muscles from day 15 to day 35 which demonstrates expression for more than four weeks after NT-3 gene transfer. No adenoviral NT-3 transcripts were detected in various other tissues with the exception of spinal cord.

At day 25, AdNT-3 injected gastrocnemius muscles deomonstrated a more than 100 fold-increase in NT-3 immunoreactivity (300 ng/g wet weight in Ad-NT-3 injected muscles vs 2.4 ng/g in uninjected animals). At the same time, NT-3 immunoreactivity was detected in the sera of AdNT-3 treated pmn-mice and exceeded by about 11 ng/ml the baseline in non-injected mice.

Figure 1:
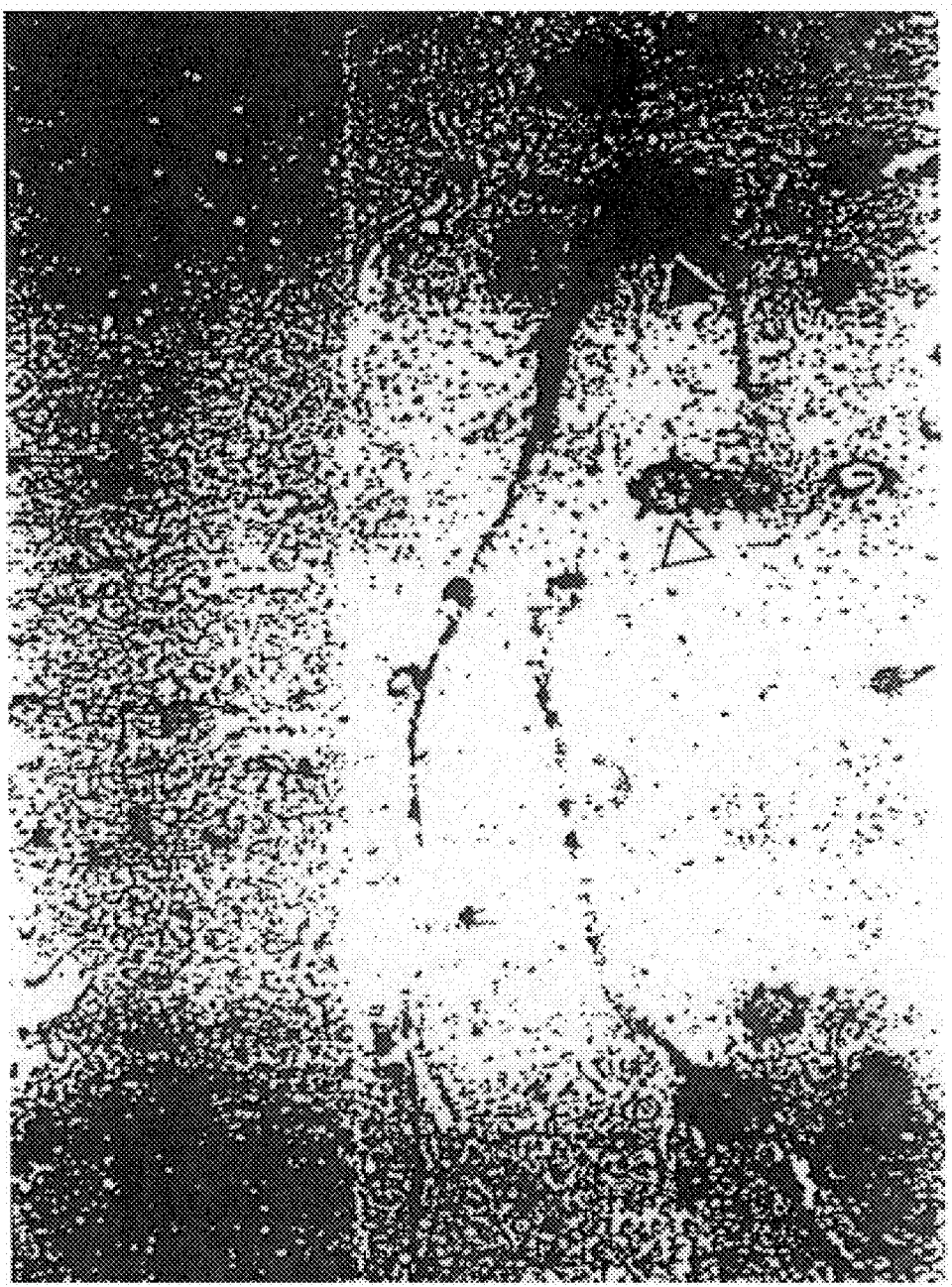
FIG. 1: β-galactosidase labelling of longitudinal sections (50 μm) of rat spinal cord at the lumbar level, after intramuscular injection of adenovirus-β-galactosidase into the gastrocnemial muscle, diffuse labelling of numerous motoneuronal cellular bodies (Δ), more intense labelling of a few motor neurons at the level of the cellular body and of the neurites, revealing the typical morphology of the motor neurons (▲).
Figure 2:
FIG. 2: identical to A, higher magnification. β-galactosidase labelling of longitudinal sections (50 μm) of rat spinal cord at the lumbar level, after intramuscular injection of adenovirus-β-galactosidase into the gastrocnemial muscle.
Figure 3:
FIG. 3: β-galactosidase-immunocytochemical co-labelling (Calcitonin Gene Related Peptide (CGRP) of longitudinal sections (50 μm) of rat spinal cord at the lumbar level, after intramuscular injection of adenovirus-β-galactosidase into the gastrocnemial muscle.
Figure 4:
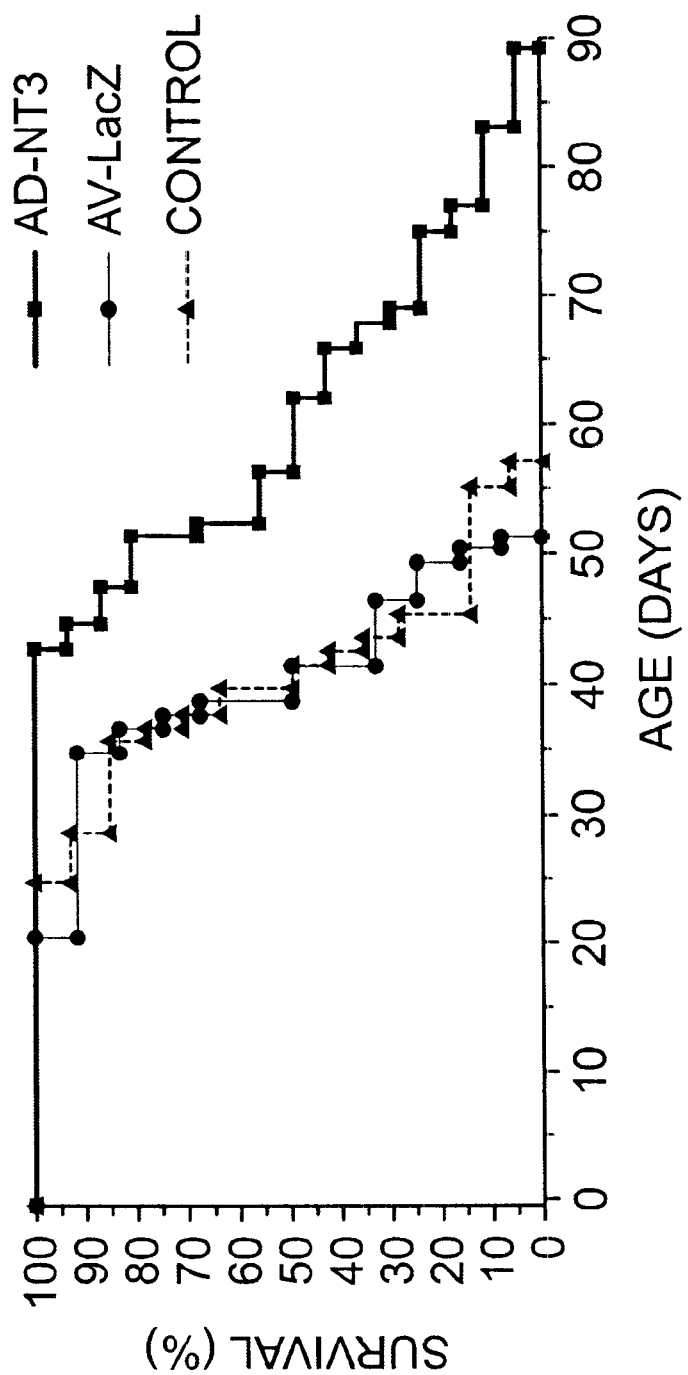
FIG. 4: Survival curves of AD-NT3 treated pmn mice.

Ad-NT3 Treatment Improves the Life Span of pmn Mice:

All non-treated pmn-mice died before day 57 and their mean survival was 40.4±2.4 days (n=14) (FIG. 4). The control vector Ad-lacZ, administered by intramuscular injection, did not modify the survival of the pmn-mice (40.0±2.5 days, n=12). In contrast, pmn-mice treated with the AdNT3 vector survived up to 89 days. Their mean lifespan was significantly improved to 61.3±2.5 days (n=16, p<0.001) which represents a 50% increase in mean lifespan. Some pmn-mice treated with a fivefold higher adenoviral dose ($5 \times 10^9$ pfu) did not show a further improvement of lifespan (49/57/61 days, mean 56 days).

Figure 5:
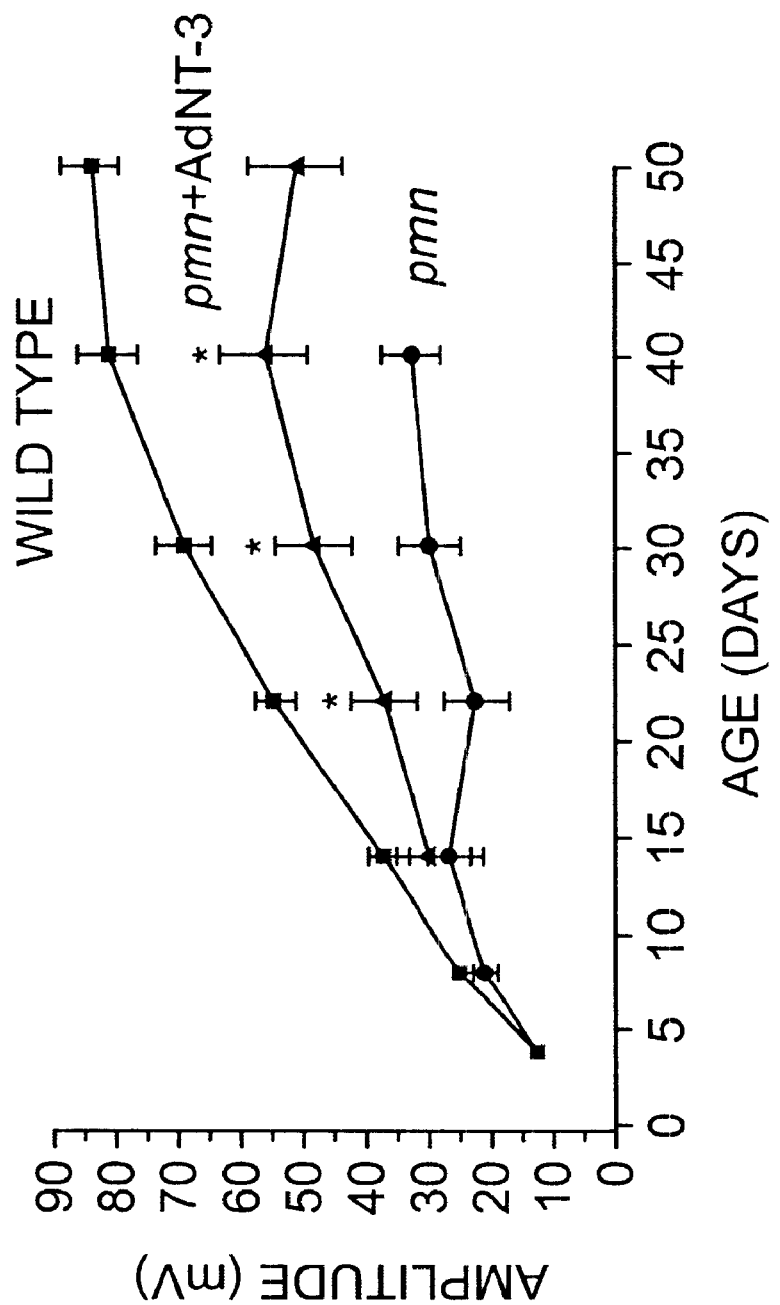
FIG. 5: Amplitude of the muscle action potential after supramaximal sciatic nerve stimulation in adenoviral treated pmn animals.

Ad-NT3 Improves Neuromuscular Function:

In order to precisely characterize the disease progression in AdNT-3 treated pmn-mice an electromyographical (EMG) study was performed, using three EMG-parameters: i) spontaneous denervation activity (fibrillations) in gastrocnemius muscle ii) amplitude of the evoked response (compound muscle action potential, CMAP) elicited by a supramaximal electrical stimulus applied to the sciatic nerves (recorded in gastrocnemius muscle), and iii) spontaneous electrical activity recorded from the diaphragm.

i) Fibrillations mark the onset of the functional denervating process; they occured before day 17 both in AdNT-3 treated pmn-mice and in non-treated pmn-mice.

ii) The amplitude of the CMAP of the gastrocnemius muscle increased with age and reached in normal mice a plateau of 80–90 mV at age 45 days. In non-treated pmn-mice a maximum of 20–30 mV corresponding to 40% of normal is reached around day 20 with no further increase (FIG. 5) presumably due to ongoing denervation. AdNT-3 treatment induced a significant recovery of the CMAP amplitude in pmn-mice: at 3 weeks it represented 70% of normal mice. The amplitudes of the CMAP in pmn mice did not differ between right and left legs of unilaterally injected mice.

iii) Because denervation of the diaphragm presumably determines the course of the disease in pmn mice, the effect of AdNT-3 treatment on the electrical activity of this muscle at day 35 was investigated. The inspiratory phase was characterized by a burst of activity whereas the expiratory phase was characterized by electrical silence. The number of positive-negative deflections ("turns") within the impulse pattern of the burst is a measure for the number of motor unit discharges. The number of "turns" per inspiratory burst was reduced by 65% in non-treated pmn-mice as compared to healthy littermates (n=4 in each group); the maximal amplitude of the bursts was the same in both groups. In pmn-mice treated with AdNT-3 the number of "turns" per burst was not significantly enhanced, but the maximal amplitude increased considerably as compared to non-treated pmn-mice (Table 1).

TABLE 1

|  | Control (n = 4) | Untreated pmn (n = 4) | NT3 treated pmn (n = 4) |
|---|---|---|---|
| Mean duration of a burst of inspiration (ms) | 138.8 ± 4.4 | 77.2 ± 7.7 ($P < 0.003$)[a] | 99.1 ± 14.1 ($P < 0.037$)[b] ($P < 0.22$)[c] |
| Mean number of turns per burst | 119.4 ± 6.0 | 40.7 ± 8.5 ($P < 0.001$)[a] | 46.9 ± 5.5 ($P < 0.001$)[b] ($P < 0.57$)[c] |
| Mean of maximal amplitude ($\mu$V) | 626 ± 95 | 695 ± 78 ($P < 0.61$)[a] | 1062 ± 70 ($P < 0.011$)[b] ($P < 0.018$)[c] |

[a]Control vs untreated pmn
[b]Control vs NT3-treated pmn
[c]Untreated pmn vs NT3-pmn It was 626+95 mV and 695+78 mV in healthy litternnates and non-treated pmn-mice, respectively, but was 1062+70 mV in AdNT-3-treated pmn-mice (p<0.02). The increase of the spike amplitude within the respiratory bursts suggests that AdNT-3 causes an increase of the size of the motor units in pmn-mice, which evidences an induction of peripheral or collateral sprouting of motor axon endings. The conclusion from electromyographical analysis was confirmed by histological analysis of endplate innervation in treated and control pmn animals.

Ad-NT3 Protects Against Axonal Degeneration

Prolonged lifespan and improved neuromuscular function of AdNT3 treated pmn mice were reflected by an increased number of phrenic nerve fibres, which innervates the diaphragm. Light micrographs at day 25 showed that the number of axons in non-treated pmn-mice and AdlacZ treated pmn-mice were reduced to 122±13 (n=6) and 120±11 (n=8), respectively, as compared to 263±8 myelinated fibres in normal littermates (n=4). The number of myelinated fibres in the phrenic nerve of AdNT3 injected pmn mice was significantly higher (164±15, n=8, P<0.05), which corresponds to a 30% reduction in the loss of myelinated fibers. At day 35, when several non-treated pmn-mice had already died, the AdNT-3 treated pmn-mice still contained more myelinated fibres (130±7, n-8) than non-treated (118±4, n=10) or AdlacZ-injected pmn-mice (115±4, n=8), albeit this difference was less pronounced than ten days earlier.

Potentiated effects of AdNT-3 and AdCNTF Cotreatment

The effect of NT-3 is enhanced by CNTF, a molecule known for its neuroprotective action in the pmn-model (Sendtner et al., Nature 373, 344–346 (1995); Sagot et al., Eur J. Neurosci. 7, 1313–1322 (1995). Mice were treated with a combination of AdNT-3 and AdCNTF, an adenoviral vector coding for a biologically active and secretable form of CNTF. The mean survival of cotreated pmn-mice (66±7.6 days, n=11, FIG. 8) tended to be higher than for each treatment alone (AdNT-3: 61.3±2.5 days, n=16; AdCNTF: 52.9±4.4 days, n=13) although this difference remains below statistical significance. All pmn-mice however that survived for more than 3 months (maximum 105 days) belonged to the AdNT-3+AdCNTF group.

At 25 days of age, animals cotreated with AdNT-3 and AdCNTF had 192±11 phrenic nerve fibers (n=8) while animals treated with AdNT-3 or AdCNTF alone had 164±15 and 167±21 (n=4) fibers, respectively (FIGS. 9 and 10). At day 35, the number in the AdNT-3+CNTF group had decreased to 157±10 (n=10), which is significantly higher than in the AdNT-3 group (130±7, p<0.05) and in the control groups (non-treated: 118±4, n=10; AdlacZ-injected: 115±4, n=8, p<0.01 respectively). Hence, at days 25 and 35, the loss of myelinated fibers was 30% and 20% smaller in animals that had received AdCNTF in addition to AdNT-3 than in animals that had received AdNT-3 only.

Treatment with AdNT-3 and AdCNTF Induces Muscle Reinnervation

The electrophysiological findings are suggestive of reinnervation phenomena in AdNT-3 treated pmn-mice.

Figure 11A:
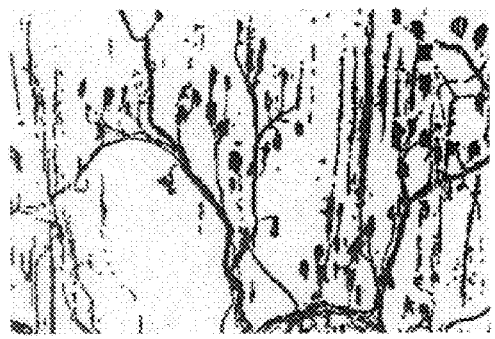
Figure 11B:
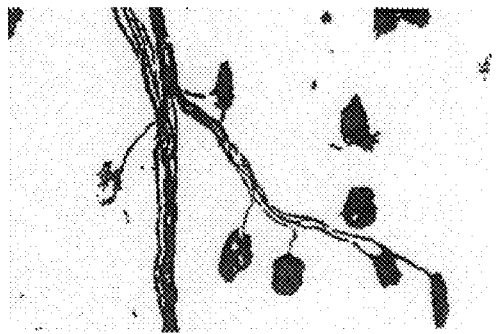
Figure 11C:
Figure 11D:
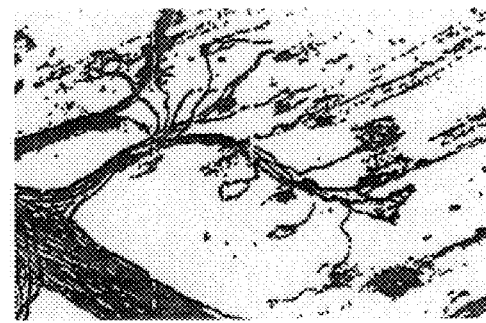

The pattern of terminal innervation in superficial gluteus muscles using an acetylcholinesterase-silver method (Namba et al., Am. J. Clin. Pathol. 47, 773–783 (1967); Gurney et al., J. Neurosci. 12, 3241–3247 (1992)) was, therefore, examined. In normal mice, a single terminal axon usually supplied one endplate (FIG. 11a and b) and only few axons branched at their last Ranvier node and supplied two endplates. In untreated pmn-mice the number of axons in intramuscular nerve branches was greatly reduced, only few bundles of terminal axons emerged from the nerves, and numerous endplates lacked axons (FIG. 11c). Endplates still connected to an axon showed the same one-to-one innervation pattern as in normal mice: both the terminal axon and its terminal branches had blunt dilatations, and the terminal branches were rarified (FIG. 11d). Argentophilic granules marked the course of degenerated axons and were also within the nerve branches. In some places fine sprouts emerged from the end of broken axons and also from Ranvier nodes, but these sprouts were thin (presumably non-myelinated) and usually did not reach an endplate. The sensory innervation of muscle spindles was preserved.

Figure 11E:
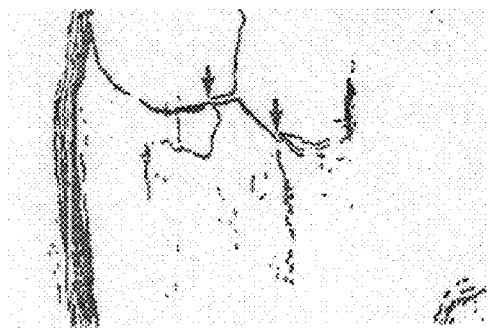
Figure 11F:
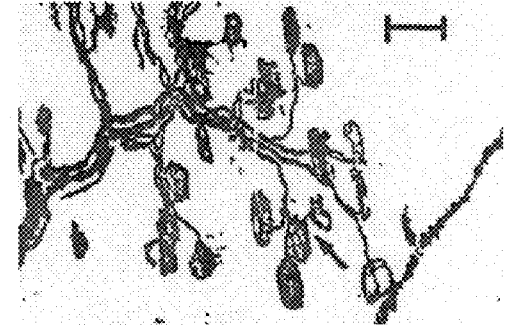

FIG. 11e shows the pattern in one out of 3 AdNT-3 treated pmn-mice. Bundles of terminal axons emerging from the branches were more prominent and the axons branched at successive Ranvier nodes and each supplied several endplates. After AdNT-3+AdCNTF treatment, analyzed in 4 pmn-mice, the endplate zone of the muscle was filled with criss-crossing axons which supplied endplates arranged in a grape-like fashion. In these mice, endplates devoid of an axon were virtually absent. Axons approaching endplates were short and most emerged from Ranvier nodes but also often, from other endplates (terminal sprouts, FIG. 11f). It was not unusual to see a terminal sprout supplying an endplate which then again had a terminal sprout supplying a second endplate.

Conclusion of the pmn Study

Intramuscular injection of an Ad-NT-3 provides a 50% increase in life span to pmn mice. The physiological mechanisms likely to be responsible for the effect of NT-3 on life span has been determined: protection of axons from degeneration, and stimulation of collateral sprouting at the level of terminal endings.

The effects of combined AdNT-3 and AdCNTF cotreatment on axonal survival and maximum lifespan of pmn-mice were more pronounced than those of AdNT-3 or AdCNTF alone. This suggests that, in pmn-mice, these two factors might act on distinct motor neuron subpopulations, be important at different stages of motor neuron degeneration or even influence differentially non-neuronal cells like muscle cells (Helgren et al., Cell 76, 493–504 (1994)) or Schwann-cells. These findings also stress the therapeutic potential of coadministering neurotrophic factors belonging to different families.

These results constitute the first demonstration of the impact of in vivo gene transfer on life span in a genetic animal model of a disease. Furthermore, this study provides a strong rationale for the use of adenoviral mediated gene therapy for motoneuronal diseases. Indeed, comparable results can not be obtained by systemic injection of recombinant NT-3 protein. Adenoviral-mediated administration of NT-3 modifies the bioavailability profile of NT-3 as compared to systemic protein administration. The protein is produced both at the post synaptic ends of neuromuscular junctions, in motor neuron cell bodies and is continuously released in the circulation.

Example 2B

Administration of Adenovirus Encoding Neurotrophic Factors into Muscle of SOD* Mice Animal Supply:

The mutant animals are supplied by Transgenic Alliance. SOD* animals present a wide variability in life span, up to 50 days differences in the life span of mice having received the same treatment at the same time. As a consequence, a large number of animals is necessary to reach statistically significant results.

General Methods

Animals were injected with different adenoviral constructs (AdNT-3, AdCNTF, AdBDNF, AdGDNF, Ad-βgal) and at different ages. The evoked motor response in the gastrocnemius muscle after supramaximal stimulation of the sciatic nerve was recorded in each animal every ten days. A comparison with riluzole was also undertaken.

Effect of Intramuscular Injection of Ad-NT3

Intramuscular injections were performed in newborn and adult animals with an adenoviral vector encoding murine NT-3 under the control of an RSV promoter. Animals were injected either at 4–5 weeks of age, just before the appearance of the first electromyographical deficits, or at 13 weeks of age at the appearance of the first clinical symptoms (Table 2).

TABLE 2

| Age of injection | Ad-NT3 | Ad-βgal | animals not injected |
|---|---|---|---|
| newborn | 163.9 ± 5.34 (n = 12)<br>$P^2$ 0.049 vs uninjected<br>$P^2$ 0.003 vs Ad-βgal | 145.17 ± 2.45 (n = 10) | 152.04 ± 3.02 (n = 24) |
| 4–5 weeks | 161.26 ± 2.86 (n = 15)<br>$P^2$ 0.045 vs uninjected<br>$P^2$ 0.048 vs Ad-βgal | 152.16 ± 3.32 (n = 18) | |
| 13 weeks | 166.9 ± 4.17 (n = 10)<br>$P^2$ 0.009 vs uninjected | N.D. | |

N.D. not determined

The data show that intramuscular injection of Ad-NT3 in SOD* mice produces an increase in life span of 9–14 days as compared to uninjected controls. The observed differences are statistically significant. Interestingly, an increase in life span is observed when animals are injected at 13 weeks, i.e. at the time of appearance of the first symptoms.

In another experiment an adenovirus encoding β-Gal or NT3 was injected to 3–4 weeks old $FALS_{G93A}$ mice, a strain of transgenic mice expressing a mutated form of human SOD (93Gly ->Ala) and displaying a progressive motoneuronal degeneration, leading to paralysia of the limbs and death within 4 to 6 months (Gurney et al., 1994).

A total of $5.10^8$ to $10^9$ pfu was injected per animal, distributed by quarter in each gastrocnemian and biceps muscle. Lethality was determined. Untreated animals lived 142.4+/−4.5 days, which is not statistically different from the Ad-B-Gal injected animals (147.8+/−3.0). However, Ad-NT3 injected animals lived for 162.86+/−5.75 days. 6 out of the 7 ad-NT3-treated animals lived even longer than the oldest non-treated animals. 5 out the same group lived longer than the oldest ad-G-Gal treated animals. These results demonstrate than im injection of a neurotrophin-expressing adenovirus can slow down disease progression in a murine model of ALS.

The evoked motor response in the gastrocnemius muscle after sciatic nerve stimulation was examined at different ages. A very large variability was observed for this parameter. A regular decrease was observed along the course of the disease in each animal (Kennel et al., 1996), but the rate and the extent of this decrease could not be correlated with life span. No significant modification of this parameter upon Ad-NT3 treatment was observed.

No significant effect on life span in SOD* mice was observed when other recombinant adenoviruses were injected intramuscularly, namely: Ad-GDNF, Ad-CNTF, Ad-BDNF injected at birth; Ad-GDNF injected at 5 or 13 weeks; combination of Ad-GDNF+Ad-BDNF or Ad-GDNF+Ad-CNTF injected at birth; or AdGDNF+Ad-CNTF injected at 5 weeks.

Effect of Riluzole:

Riluzole is an FDA approved therapy for ALS. Riluzole has also been shown to delay median time to death in a transgenic mouse model of ALS. These mice express human superoxide dismutase bearing one of the mutations found in one of the familial forms of human ALS. Riluzole is a member of the benzothiazole class. Chemically, riluzole is 2-amino-6-(trifluoromethoxy)-benzothiazole.

The effect of riluzole on SOD* mice was tested in three different protocols. p.o. administration of 4 and 8 mg/day/kg to SOD* mice from the 5th week of age, produced no effect on life span.

Riluzole was delivered in the drinking water of SOD* mice at a concentration of 100 μg/ml, a condition reported to produce a 13 days increase in human patient life span (Gurney et al., Pathogenic mechanisms in familial amyotrophic lateral sclerosis due to mutation of Cu,Zn superoxyde dismutase. Path Biol., 44, 51–56, 1996). This corresponds to an approximate dose of 20–25mg/kg/day, at which no effect on life span of the SOD* mice was observed (treated animals 151.8+6.26, n=11).

Conclusion

Riluzole at concentrations ranging from 2.5 to 16 times those effective in human clinic (100 mg/patient/day, i.e. approx 1.5 mg/kg/day)produced no effect on SOD* mice life span. This suggests that SOD* mice represents a severe form of human ALS. This finding is reinforced by the fact that SOD* mice represent a model for familial ALS, which is thought to have an earlier onset and a poorer prognosis than sporadic forms (Rowland, Amyotrophic lateral sclerosis: Human challenge for neuroscience. Proc. Natl. Acad. Sci. USA, 92, 1251–1253, 1995; Gurney et al., 1996).

The data show that Ad-NT3 injected intramuscularly in SOD* mice produces increase in life span in the range of 9–14 days as compared to controls. This increase was significant. Three interesting features must be noted:

a) Increase in life span was observed when injection was performed in adult mice displaying the first clinical signs of the disease.
b) No therapeutic or life span increase was observed after the injection of NT3 protein into SOD* mice. Therefore, as for pmn mice, the results demonstrate the advantages of the delivery of therapeutic proteins through gene transfer.
c) No increase of SOD* mice life span could be observed in our hands with riluzole. This suggests that any treatment producing an increase in life span in SOD* mice can be predicted to produce a better effect than riluzole in human patients.

Therapeutic effects may also be obtained by using intrathecal administration (see WO94/08026), or with viruses expressing other trophic factors.

Example 3

Intramuscular Administration of Naked DNA

The data using pmn or SOD* mice show that intramuscular injection of recombinant adenovirus expressing a trophic factor can produce therapeutic effect in these animals. The observed effects may be linked to retrograde infection of motor neurons and to trophic factor expression in the spinal cord. Alternatively, the trophic factor could exert its activity after being released in the circulation from the infected muscle. In this case, any efficient method for neurotrophic gene transfer in muscle could produce beneficial effects similar to those observed with adenoviral infection.

Gene transfer in skeletal muscle can be achieved after by direct injection of naked DNA (Wolff et al., Direct gene transfer into mouse muscle in vivo. Science, 247, 1465–1468, 1990). Several examples of intramuscular transfer of genes encoding secreted proteins have been published, where the level of transgene expression was sufficient to produce a physiological effect. A study of the potential therapeutic potential of naked DNA transfer for motoneuronal disorders has been undertaken.

Comparison of Transgene Expression Levels After Ad and Naked DNA Injection.

Mouse gastrocnemius muscle has been injected with a recombinant adenovirus encoding luciferase (AdCMVLuc) or a plasmid expressing the same transgene (pCMVLuc), under the control of a CMV promoter. After injection of $10^9$ pfu of AdCMVLuc, 100–300 pg of luciferase was detected in the injected muscle. This value was comparable to that observed after injection of pCMVLuc (FIG. 7, Panel a). However the variability within a group was much higher when using naked DNA when compared to the adenoviral vector. Indeed, a difference of 2–3 logs in transgene expression levels where typically observed when using naked DNA, while the variations where within the order of 1 log when using adenoviruses.

Analysis of Parameters Potentially Influencing Gene Transfer/Expression Efficiency:

Promotor RSV/CMV: RSV and CMV promoters provided comparable transgene expression when used in newborn mice. When injected in adult animals, the RSV promoter lead to a level of luciferase expression that was more than 10-fold lower than that observed with CMV 72 hours after injection. However, 30 days after injection similar levels were observed with the two constructs (FIG. 7, Panels c and d).

Age at injection: Injection in adult or newborn animals produced comparable levels of transgene expression when the sacrifice was performed 30 days after injection. In contrast, when sacrifice was performed 72 hours after injection, the levels of RSV driven luciferase expression were more than 10 times higher in newborn than adults, while the contrary was observed with a CMV promoter (FIG. 7).

Batch preparation: A ten-fold difference in luciferase expression can be observed between two different experimental batches of the same plasmid, prepared using standard commercial kits (FIG. 7). In contrast, the levels of transgene expressed when using different batches prepared by the production team were constant (not shown). This stresses the need for controlled conditions of plasmid preparations.

Muscle injected, sex, mode of injection: No major difference depending on muscle injected (triceps vs gastrocnemius), sex or mode of injection (transcutaneous vs surgery) was observed.

Conclusion of the Naked DNA Experiments

The results show that intramuscular injection of naked DNA produces transgene expression levels comparable to that observed after intramuscular injection of adenovirus. However interanimal variability is much higher with naked DNA than with adenoviruses. The data also stress the need for controlled production of plasmid to be injected.

All the references discussed herein are incorporated by reference.

One skilled in the art will readily appreciate the present invention is well adapted to carry out the objects and obtain the ends and advantages mentioned, as well as those inherent therein The peptides, polynucleotides, methods, procedures and techniques described herein are presented as representative of the preferred embodiments, and intended to be exemplary and not intended as limitations on the scope of the present invention. Changes therein and other uses will occur to those of skill in the art which are encompassed within the spirit of the invention or defined by the scope of the appended claims.

What is claimed is:

1. A method of muscle reinnervation and of inducing peripheral or collateral sprouting of motor axon endings in a mammal comprising administering directly to muscle tissue at least one nucleic acid encoding at least one neurotrophic factor chosen from NT-3 and CNTF, wherein said at least one nucleic acid is operably linked to a promoter, and wherein expression of said nucleic acid sequence in said mammal results in increased innervation of muscle tissue of the same medullary level as the muscle tissue that was administered the nucleic acid, increased peripheral sprouting of motor axon endings, increase collateral sprouting of motor endings, or combinations thereof.

2. A method according to claim 1, for the treatment of an impairement of nervous system.

3. A method according to claim 2, wherein the impairement is nerve damage.

4. A method according to claim 2, wherein the impairement is a neurodegenerative disease.

5. A method according to claim 4, wherein the disease is amyotrophic lateral sclerosis or spinal muscular atrophy of infancy.

6. A method according to claim 1, wherein the nucleic acid is inserted in a vector.

7. A method according to claim 6, wherein the vector is an adenovirus, retrovirus, herpes virus or adeno-associated virus.

8. A method according to claim 7, wherein the vector is a replication defective virus.

9. A method according to claim 8, wherein the virus is of human origin.

10. A method according to claim 8, wherein the virus is of animal origin.

11. A method according to claim 8, wherein the virus is an adenovirus lacking all or part of the E1 region, and all or part of either or both of the E3 or E4 region of the adenovirus genome.

12. A method according to claim 11, wherein the nucleic acid is inserted into the genome of the adenovirus within the E1, E3 or E4 region.

13. A method according to claim 1, wherein the nucleic acid is a naked DNA.

14. A method according to claim 1, wherein the nucleic acids are administered to muscles of the upper limbs.

15. A method according to claim 14, wherein said muscles are either or both of biceps or triceps.

16. A method according to claim 1, wherein the nucleic acids are administered to muscles of the thorax.

17. A method according to claim 16, wherein said muscles are pectoral muscles.

18. A method according to claim 1, wherein nucleic acids are administered to muscles of the lower limbs.

19. A method according to claim 18, wherein said muscles are gastrocnemial muscles.

20. A method according to claim 1, wherein said administering comprises injection at several points of the same muscle.

21. A method according to claim 1, comprising administering said at least one nucleic acid to muscle tissue proximate to the site of a nerve linkage associated with a chosen medullary functional level, wherein said nucleic acid is delivered to said motor neurons and expressed.

22. A method of producing at least one neuroactive substance in mammalian motor neurons comprising administering directly to muscle tissue at least one nucleic acid encoding at least one neurotrophic factor chosen from NT-3 and CNTF, wherein said at least one nucleic acid is operably linked to a promoter, and wherein expression of said nucleic acid sequence in said mammal results in increased innervation of muscle tissue of the same medullary level as the muscle tissue that was administered the nucleic acid, increased peripheral sprouting of motor axon endings, increase collateral sprouting of motor axon ending, or combinations thereof.

23. A method according to claim 22, wherein said neuroactive substance is produced at the post synaptic ends of neuromuscular junctions.

24. A method according to claim 22, wherein said motor neurons are afferent motor neurons and said nucleic acid is expressed in the spinal cord.

25. A method according to any one of claims 1 or 22, wherein said at least one nucleic acid encodes both neurotrophin-3 and CNTF.

26. A method of treating an impairment of the nervous system, comprising administering directly to muscle tissue at least one nucleic acid encoding at least one neurotrophic factor chosen from NT-3 and CNTF, wherein said at least one nucleic acid is operably linked to a promoter, and wherein expression of said nucleic acid sequence in said mammal results in increased innervation of muscle tissue of the same medullary level as the muscle tissue that was administered the nucleic acid, increased peripheral sprouting of motor axon endings, increase collateral sprouting of motor axon endings, or combinations thereof.

27. A method according to claim 26, wherein the nucleic acids are a naked DNA encoding neurotrophin-3 and a naked DNA encoding CNTF.

28. A method according to claim 26, wherein said nucleic acids are inserted separately into a first and a second replication defective adenovirus.

29. A composition useful for muscle reinnervation and for inducing the sprouting of motor axons endings comprising a first viral vector comprising a nucleic acid encoding CNTF operably linked to a promoter and a second viral vector comprising a nucleic acid encoding NT-3 operably linked to a promoter.

30. The composition of claim 29, for the treatment of an impairment of nervous system.

31. The composition of claim 30, wherein the impairment is nerve damage.

32. The composition of claim 30, wherein the impairment is a neurodegenerative disease.

33. The composition of claim 32, wherein the disease is amyotrophic lateral sclerosis or spinal muscular atrophy of infancy.

34. The composition of claim 29, wherein the first and second viral vectors are independently adenoviruses, retroviruses, herpes viruses or adeno-associated viruses.

35. The composition of claim 29, wherein at least one of the first and second viral vectors is a replication defective virus.

36. The composition of claim 35, wherein the replication defective virus is of human origin.

37. The composition of claim 35, wherein the replication defective virus is of animal origin.

38. The composition of claim 29, wherein both the first and second viral vectors are adenoviruses which independently lack all or part of the E1 region, and all or part of either or both of the E3 or E4 region of the adenovirus genome.

39. The composition of claim 38, wherein said nucleic acids are independently inserted into the genome of the adenovirus within the E1, E3 or E4 region.

40. The composition of claim 29, wherein said nucleic acids are administered to muscles of the upper limbs.

41. The composition of claim 40, wherein said muscles are either or both of biceps or triceps.

42. The composition of claim 29, wherein said nucleic acids are administered to muscles of the thorax.

43. The comoosition of claim 42, wherein said muscles are pectoral muscles.

44. The composition of claim 29, wherein the nucleic acids are administered to muscles of the lower limbs.

45. The composition of claim 44, wherein said muscles are gastrocnemial muscles.

* * * * *